(12) United States Patent
Bertolero et al.

(10) Patent No.: US 6,849,075 B2
(45) Date of Patent: Feb. 1, 2005

(54) CARDIAC ABLATION DEVICES AND METHODS

(75) Inventors: Art Bertolero, Danville, CA (US); Tamer Ibrahim, Oakland, CA (US); Daniel J. Conley, Santa Rosa, CA (US)

(73) Assignee: Estech, Inc., Danville, CA (US)

( * ) Notice: Subject to any disclaimer, the term of this patent is extended or adjusted under 35 U.S.C. 154(b) by 116 days.

(21) Appl. No.: 10/272,446

(22) Filed: Oct. 15, 2002

(65) Prior Publication Data
US 2003/0120268 A1 Jun. 26, 2003

Related U.S. Application Data

(60) Provisional application No. 60/337,070, filed on Dec. 4, 2001.

(51) Int. Cl.[7] .............................................. A61B 18/18
(52) U.S. Cl. ........................ 606/41; 128/898; 607/130
(58) Field of Search ...................... 606/41–50; 607/101, 607/102, 116, 122, 130; 128/898; 600/374

(56) References Cited

U.S. PATENT DOCUMENTS

| | | | |
|---|---|---|---|
| 6,237,605 B1 * | 5/2001 | Vaska et al. ................ | 128/898 |
| 6,251,065 B1 | 6/2001 | Kochamba et al. | |
| 6,346,077 B1 * | 2/2002 | Taylor et al. ............... | 600/204 |
| 6,463,332 B1 * | 10/2002 | Aldrich ...................... | 607/101 |
| 6,511,416 B1 | 1/2003 | Green, II et al. | |
| 6,514,250 B1 * | 2/2003 | Jahns et al. .................... | 606/41 |
| 6,522,905 B2 | 2/2003 | Desai | |
| 6,527,767 B2 * | 3/2003 | Wang et al. .................. | 606/32 |
| 6,544,263 B2 | 4/2003 | Morgan et al. | |
| 6,652,518 B2 * | 11/2003 | Wellman et al. .............. | 606/41 |

* cited by examiner

*Primary Examiner*—Roy D. Gibson
(74) *Attorney, Agent, or Firm*—Townsend and Townsend and Crew LLP

(57) ABSTRACT

Devices and methods provide for ablation of cardiac tissue for treating cardiac arrhythmias such as atrial fibrillation. Although the devices and methods are often be used to ablate epicardial tissue in the vicinity of at least one pulmonary vein, various embodiments may be used to ablate other cardiac tissues in other locations on a heart. Devices generally include at least one tissue contacting member for contacting epicardial tissue and securing the ablation device to the epicardial tissue, and at least one ablation member for ablating the tissue. Various embodiments include features, such as suction apertures, which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive introducer devices and the like. Although devices and methods of the invention may be used to ablate epicardial tissue to treat atrial fibrillation, they may also be used in veterinary or research contexts, to treat various heart conditions other than atrial fibrillation and/or to ablate cardiac tissue other than the epicardium.

74 Claims, 11 Drawing Sheets

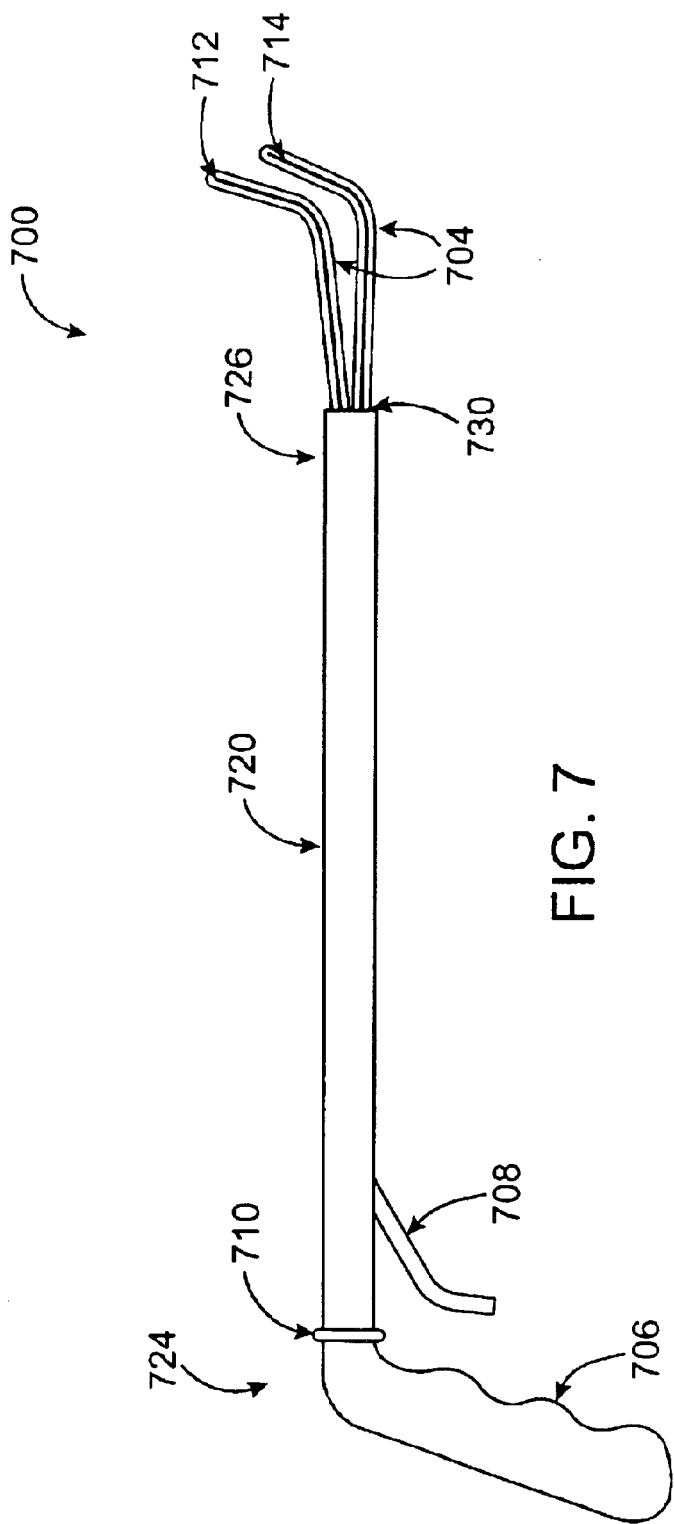
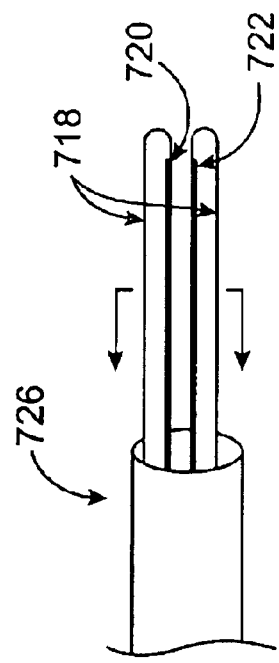
FIG. 7
FIG. 7a

CARDIAC ABLATION DEVICES AND METHODS

CROSS-REFERENCES TO RELATED APPLICATIONS

The present application claims priority to U.S. Provisional Patent Application Ser. No. 60/337,070, filed Dec. 4, 2001, entitled "Methods and Devices for the Least Invasive Cardiac Surgery of Atrial Fibrillation," the entire contents of which is hereby incorporated by reference.

BACKGROUND OF THE INVENTION

The present invention relates generally to medical devices and methods. More specifically, the invention relates to devices and methods for ablating epicardial tissue to treat cardiac arrhythmias such as atrial fibrillation.

Atrial fibrillation (AF) is a heart beat rhythm disorder (or "cardiac arrhythmia") in which the upper chambers of the heart known as the atria quiver rapidly instead of beating in a steady rhythm. This rapid quivering reduces the heart's ability to properly function as a pump. AF is characterized by circular waves of electrical impulses that travel across the atria in a continuous cycle. It is the most common clinical heart arrhythmia, affecting more than two million people in the United States and some six million people worldwide.

Atrial fibrillation typically increases the risk of acquiring a number of potentially deadly complications, including thrombo-embolic stroke, dilated cardiomyopathy and congestive heart failure. Quality of life is also impaired by common AF symptoms such as palpitations, chest pain, dyspnea, fatigue and dizziness. People with AF have, on average, a five-fold increase in morbidity and a two-fold increase in mortality compared to people with normal sinus rhythm. One of every six strokes in the U.S. (some 120,000 per year) occurs in patients with AF, and the condition is responsible for one-third of all hospitalizations related to cardiac rhythm disturbances (over 360,000 per year), resulting in billions of dollars in annual healthcare expenditures.

AF is the most common arrhythmia seen by physicians, and the prevalence of AF is growing rapidly as the population ages. The likelihood of developing AF increases dramatically as people age; the disorder is found in about 1% of the adult population as a whole, and in about 6% of those over age 60. By age 80, about 9% of people (one in 11) will have AF. According to a recent statistical analysis, the prevalence of AF in the U.S. will more than double by the year 2050, as the proportion of elderly increases. A recent study called The Anticoagulation and Risk Factors in Atrial Fibrillation (ATRIA) study, published in the Spring of 2001 in the Journal of the American Medical Association (JAMA), found that 2.3 million U.S. adults currently have AF and this number is likely to increase over the next 50 years to more than 5.6 million, more than half of whom will be age 80 or over.

As the prevalence of AF increases, so will the number of people who develop debilitating or life-threatening complications, such as stroke. According to Framingham Heart Study data, the stroke rate in AF patients increases from about 3% of those aged 50–59 to more than 7% of those aged 80 and over. AF is responsible up to 35% of the strokes that occur in people older than age 85.

Efforts to prevent stroke in AF patients have so far focused primarily on the use of anticoagulant and antiplatelet drugs, such as warfarin and aspirin. Long-term warfarin therapy is recommended for all AF patients with one or more stroke risk factors, including all patients over age 75. Studies have shown, however, that warfarin tends to be underprescribed for AF. Despite the fact that warfarin reduces stroke risk by 60% or more, only 40% of patients age 65–74 and 20% of patients over age 80 take the medication, and probably fewer than half are on the correct dosage. Patient compliance with warfarin is problematic, and the drug requires vigilant blood monitoring to reduce the risk of bleeding complications.

Electrophysiologists classify AF by the "three Ps": paroxysmal, persistent, or permanent. Paroxysmal AF—characterized by sporadic, usually self-limiting episodes lasting less than 48 hours—is the most amenable to treatment, while persistent or permanent AF is much more resistant to known therapies. Researchers now know that AF is a self-perpetuating disease and that abnormal atrial rhythms tend to initiate or trigger more abnormal rhythms. Thus, the more episodes a patient experiences and the longer the episodes last, the less chance of converting the heart to a persistent normal rhythm, regardless of the treatment method.

AF is characterized by circular waves of electrical impulses that travel across the atria in a continuous cycle, causing the upper chambers of the heart to quiver rapidly. At least six different locations in the atria have been identified where these waves can circulate, a finding that paved the way for maze-type ablation therapies. More recently, researchers have identified the pulmonary veins as perhaps the most common area where AF-triggering foci reside. Technologies designed to isolate the pulmonary veins or ablate specific pulmonary foci appear to be very promising and are the focus of much of the current research in catheter-based ablation techniques.

Although cardiac ablation devices and methods are currently available, many advances may still be made to provide improved devices and methods for ablating epicardial tissue to treat AF and other arrhythmias. For example, currently available devices can be difficult to position and secure on epicardial tissue to perform an ablation. Devices such as bipolar ablation clamps and others can ablate tissue only in very limited patterns, such as one or two straight lines. Ablation devices often have no means for shielding ablative energy, to avoid unwanted burning of tissues in the vicinity of the heart, such as the esophagus. Relatively few devices can be secured to epicardial tissue with sufficient force to allow for stabilization of the heart. And many ablation devices may not be introduced by minimally invasive means, thus requiring an open surgical procedure. Typically, therefore, current cardiac ablation procedures for AF treatment still require stopping the heart and using a cardiopulmonary bypass apparatus.

Therefore, a need exists for improved devices and methods for ablating epicardial tissue to treat AF and other cardiac arrhythmias. Preferably, such devices and methods would provide ablation adjacent to and/or encircling one or more pulmonary veins, to disrupt conduction pathways and thus partially or completely treat AF. Also preferably, such devices and methods would allow for minimally invasive ablation procedures, in some cases on a beating heart. Such devices might also provide additional advantages, such as advantageous ablation patterns, shielding of ablative energy and/or the like. At least some of these objectives will be met by the present invention.

BRIEF SUMMARY OF THE INVENTION

Devices and methods of the present invention provide for ablation of cardiac tissue for treating cardiac arrhythmias such as atrial fibrillation. Although the devices and methods are often be used to ablate epicardial tissue in the vicinity of at least one pulmonary vein, various embodiments may be used to ablate other cardiac tissues in other locations on a heart. Generally, devices of the invention include a tissue contacting member for contacting a portion of the epicardial tissue of a heart and securing the ablation device to the epicardial tissue, and an ablation member for ablating at least a portion of the tissue. In various embodiments, the devices have features which enable the device to attach to the epicardial surface with sufficient strength to allow the tissue to be stabilized via the device. For example, some embodiments may be used to stabilize a beating heart to enable a beating heart ablation procedure. Many of the devices may be introduced into a patient via minimally invasive incisions, introducer devices and the like. Although much of the following description focuses on using devices and methods of the invention to treat atrial fibrillation (AF) by ablating epicardial tissue on a human heart, the devices and methods may be used in veterinary or research contexts, to treat various heart conditions other than atrial fibrillation and/or to ablate cardiac tissue other than the epicardium.

In one aspect, a method for ablating epicardial tissue on a heart of a patient to treat a cardiac arrhythmia includes first contacting epicardial tissue with an ablation device having at least one tissue contacting member coupled with at least one ablation member. The ablation device is then positioned on the epicardial tissue in a position adjacent to at least one pulmonary vein for ablating the tissue to treat the arrhythmia. Sufficient suction force is applied through the at least one tissue contacting member to secure the contacting member to the tissue and to cause the at least one ablation member to directly contact the tissue. Finally, ablation energy is applied to at least a portion of the epicardial tissue with the at least one ablation member to disrupt one or more conduction pathways in the heart.

Optionally, the step of contacting the epicardial tissue may include contacting tissue at least partially encircling at least one pulmonary vein. In some embodiments, in fact, the ablation device contacts epicardial tissue at least partially encircling two pulmonary veins. For example, one superior and one inferior vein on the same side of the heart may be at least partially encircled. In another embodiment, both inferior or both superior veins may be at least partially encirdled. In other embodiments, two pulmonary veins are completely encircled. In still other embodiments, all four pulmonary veins are at least partially encircled. In any such encircling embodiments, a portion of the ablation device may be steered to provide the encircling configuration. Optionally, the method may further include ablating cardiac tissue beneath the epicardial tissue. For example, one embodiment includes ablating a transmural lesion.

Optionally, the method may further include advancing the device through a minimally invasive introducer device to a location near the epicardial tissue to be ablated. The method may also include positioning the ablation device in a position for contacting the epicardial tissue, using at least one positioning device. For example, in some embodiments the positioning device may include at least one flexible positioning arm and the positioning step may include positioning the surgical device with the arm and applying tensile force to the arm to rigidify the arm.

In some embodiments, the method further includes viewing the epicardial tissue with an imaging device coupled with the ablation device. In other embodiments, the method includes positioning an insufflation device between the epicardial tissue and a layer of pericardial tissue and introducing an insufflation medium into the insufflation device to create a space between the epicardial tissue and the pericardial tissue. Creating a space between the epicardium and pericardium may provide for improved visualization and/or manipulation of one or more devices. In some embodiments, the insufflation medium will be carbon dioxide, air, helium or a liquid. The method may further include positioning an imaging device within the space to view the epicardial tissue.

Generally, the ablation member may be any suitable device (or multiple devices) for ablating tissue. For example, in various embodiments the ablation member may be a radio frequency device, a cryogenic device, an ultrasound device, a laser device, a thermo-electric chip device, a chemical agent delivery device, a biological agent delivery device, a light-activated agent device, a thermal device, a microwave device, or an ablating drug delivery device. In some embodiments, for example, the ablation member comprises at least two bipolar radio frequency electrodes. In other embodiments, the ablation member comprises at least one unipolar radio frequency electrode.

Optionally, methods of the present invention may further include grasping the epicardial tissue adjacent at least one pulmonary vein with the tissue contacting member, with the contacting member comprising a pair of opposable jaws. In these embodiments, ablating the epicardial tissue may involve applying radiofrequency energy through at least one pair of bipolar electrodes, a first electrode being coupled with a first opposable jaw and a second electrode being coupled with a second opposable jaw. Alternatively, other forms of energy may be applied for ablation.

In some embodiments, suction may be used to maintain contact between the ablation member and the epicardial tissue in a location so as to maintain a margin of safety away from one or more pulmonary veins. Suction force may optionally be applied in an amount sufficient to cause the tissue contacting member to dissect through at least one layer of fat disposed between the tissue contacting member and the epicardium. Optionally, an adhesive surface on the tissue contacting member may be used for further securing the ablation device to the epicardial tissue.

In some embodiments, the method further includes stabilizing the heart using the ablation device. For example, stabilizing the heart may involve securing the ablation device to the epicardial tissue with sufficient to maintain the tissue in a position to perform an ablation procedure while the heart is beating. Securing the tissue with sufficient force, for example, may comprise creating a suction force. Additionally, securing the tissue may further comprise creating a frictional force between at least one textured surface of the tissue contacting member and the epicardial tissue.

Some embodiments of the method further include sensing an amount of ablation of the epicardial tissue, using at least one sensor coupled with the tissue contacting member so as to contact the epicardial tissue. Sensing may include, for example, transmitting a radio frequency signal across an area of ablated tissue with at least one transmitting sensor and receiving the radio frequency signal with at least one receiving sensor. Optionally, the at least one transmitting sensor and the at least one receiving sensor may comprise pairs of transmitting and receiving sensors disposed along at least part of the tissue contacting member.

In still other embodiments, methods of the invention may include cooling at least a portion of the epicardial tissue, using at least one cooling member coupled with the tissue contacting member so as to contact the epicardial tissue.

Generally, such cooling involves introducing a cooling substance into the cooling member. In another embodiment, the method includes using drug delivery means coupled with the tissue contacting member to deliver at least one drug to the epicardial tissue to enhance treatment of the cardiac arrhythmia.

In another aspect of the invention, a method for ablating epicardial tissue on a heart of a patient to treat a cardiac arrhythmia includes first advancing an ablation device through a first minimally invasive incision on the patient. The device is then contacted with a portion of the epicardial tissue directly adjacent to at least one pulmonary vein. Then, securing means on the ablation device are used to secure the ablation device to the portion of epicardial tissue. Finally, the epicardial tissue is ablated in a desired pattern so as to reduce or eliminate the cardiac arrhythmia. Optionally, this method may further comprise stabilizing the epicardial tissue using the ablation device. Also optionally, the method may include advancing a positioning device to a location near the epicardial tissue through a second minimally invasive incision and positioning the ablation device on the epicardial tissue using the positioning device.

In yet another aspect of the present invention, a device for ablating epicardial tissue on a heart of a patient to treat a cardiac arrhythmia includes at least one tissue contacting member having at least one tissue contacting surface for contacting the epicardial tissue directly adjacent to at least one pulmonary vein. At least one suction aperture is disposed along the tissue contacting surface for securing the ablation device to the epicardial tissue. At least one ablation member is coupled with the tissue contacting member for ablating the epicardial tissue to reduce or eliminate the cardiac arrhythmia. In some embodiments, the tissue contacting member contacts the epicardial tissue at least partially encircling at least one pulmonary vein. In other embodiments, the tissue contacting member at least partially encircles two pulmonary veins.

In some embodiments, the ablation device further includes a malleable support member coupled with the tissue contacting member. The malleable support member may optionally include at least one protrusion for removably attaching the support member to a positioning device.

In some embodiments, the at least one tissue contacting member further includes at least one suction port for removably connecting the tissue contacting member to a source of suction and at least one suction lumen disposed between the at least one suction port and the at least one suction aperture such that suction force applied at the port is transmitted to the aperture. In some embodiments, the tissue contacting surface further includes a textured surface for enhancing contact of the tissue contacting member with the epicardial tissue. Also in some embodiments, the tissue contacting member comprises two tissue contacting members, each having a tissue contacting surface, a plurality of suction apertures disposed along the surface and at least one suction port. In some embodiments, the two tissue contacting members are coupled with a U-shaped support member. In other embodiments, the suction apertures on each tissue contacting member are disposed in a line parallel to a longitudinal axis of each contacting member. In other embodiments, the suction apertures on each tissue contacting member are disposed in two lines parallel to, and on either side of, the ablation member. In some embodiments, each tissue contacting member optionally includes at least one vessel attachment sidearm for securing a coronary artery.

The ablation member, in some embodiments, is disposed adjacent at least one suction aperture. Some suction apertures are optionally configured to allow a portion of the epicardial tissue to be drawn into the aperture when suction is applied. Drawing tissue into a suction aperture may improve ablation capabilities of the device. In other embodiments sufficient suction force may be used to cause the ablation device to dissect through a layer of fat disposed between the tissue contacting member and the epicardial tissue. Again, such dissection may improve ablation results.

In addition to the at least one suction aperture, some embodiments include at least one adhesive. Either with or without adhesive, in some embodiments the ablation device may be secured to the epicardial tissue with sufficient force to allow the device to stabilize the heart in a desired position. In some embodiments, the attachment force is sufficient to stabilize the heart while it is beating, allowing for beating-heart ablation procedures.

In another embodiment, the tissue contacting member includes a flexible elongate membrane having a plurality of suction apertures disposed along a surface of the membrane, at least one suction lumen in fluid communication with the suction apertures, and at least one suction port for connecting the at least one suction lumen with a source of suction. For example, the plurality of suction apertures may be disposed in two parallel rows along the surface of the membrane, and the ablation member may comprise a linear ablation member positioned on the surface between the two rows of suction apertures. In another embodiment, the plurality of suction apertures is disposed in one row along the surface of the membrane, and the ablation member comprises a linear ablation member positioned on the surface along the row.

The ablation member may be coupled with the tissue contacting member in any suitable configuration, but in some embodiments the ablation member is disposed within the tissue contacting surface so as to directly contact the epicardial tissue. In some embodiments, the ablation member comprises an energy transmission member for transmitting energy from an energy source. The energy source may include, for example, radio frequency energy, ultrasound energy, microwave energy, cryogenic energy, thermoelectric energy and/or laser energy. The ablation member may have any desired shape but in one configuration is U-shaped so as to contact epicardial tissue at least partially encircling one or more pulmonary veins. Optionally, the ablation member further comprises at least one partially retractable member such that when the retractable member is deployed the ablation member contacts epicardial tissue encircling two pulmonary veins. In other embodiments, the ablation member comprises at least one linear ablation member for ablating a linear pattern on epicardial tissue. When using such a pattern, the linear ablation member may optionally include at least two overlapping members. Additionally, the at least one linear ablation member may comprise a plurality of members, each controllable on a separate radio frequency channel. In other embodiments, the ablation member includes multiple thermoelectric chips disposed in a pattern on the tissue contacting member.

Some devices according to the present invention include at least one sensor for sensing ablation of the tissue. For example, the at least one sensor may sense an electrical depolarization in heart tissue. Such a sensor may be, for example, a thermal sensor, an electrical sensor, a thermoelectric sensor, a microchip or an ultrasound sensor. In some embodiments, the at least one sensor comprises at least one pair of sensors, each pair of sensors positioned on opposite sides of the at least one ablation member. Each pair of sensors, in turn, may include a first sensor for transmitting a signal across an area of tissue to be ablated and a second sensor for receiving the signal from the first sensor.

Some embodiments will also include at least one cooling member for decreasing heat in the epicardial tissue generated by the ablation member. The cooling member may comprise, for example, a hollow member adjacent the ablation member at least one port coupled with the hollow member for allowing introduction of one or more cooling fluids into the hollow member. In some embodiments, the hollow member comprises a tubular member. In others, the hollow member comprises a chamber. The at least one port may comprise at least one inlet port for allowing the introduction of one or more cooling fluids and at least one outlet port for allowing egress of the one or more cooling fluids from the hollow tubular member. In some embodiments, the cooling member comprises a plurality of fluid outlet ports disposed along the tissue contacting member for allowing passage of fluid from the ablation device and at least one fluid introduction port coupled with the fluid outlet ports for allowing introduction of one or more cooling fluids.

Devices of the present invention may also include visualization means coupled with the device for enhancing visualization of an area around the epicardial tissue to be ablated. Some devices may include drug delivery means coupled with the tissue contacting member for delivering one or more drugs to the epicardial tissue to enhance treatment of the cardiac arrhythmia.

In still another aspect of the present invention, a device for ablating epicardial tissue on a heart of a patient to treat a cardiac arrhythmia includes at least one elongate shaft having a proximal end and a distal end, a jaw member hingedly coupled with the shaft near the distal end for grasping the epicardial tissue, at least one ablation member coupled with the jaw member, and at least one actuator on the shaft near the proximal end for opening and closing the jaw member and activating the ablation member to ablate the epicardial tissue.

As with the above-described embodiments, the ablation member may use any suitable energy source for ablating tissue. In one embodiment, for example, the ablation member comprises a bipolar radio frequency device coupled with the jaw member. The jaw member and the ablation member may be shaped to contact and ablate the epicardial tissue in a pattern such as, but not limited to, a U-shaped pattern, an L-shaped pattern, a circular pattern or a linear pattern. In various embodiments, the shaft may be malleable, may articulate about at least one joint and/or may be steerable for positioning the device. In some embodiments, the ablation member is further coupled with the shaft.

Optionally, the device may further include an insulation member at least partially surrounding the device to protect body structures in the vicinity of the epicardial tissue to be ablated from damage due to heat or electrical current. Also optionally, the ablation member may be adjustable to deliver two or more varying amounts of ablative energy to two or more locations on the epicardial tissue. Various embodiments may further include at least one sensor for sensing a quantity of ablation provided by the ablation member to the tissue. The at least one sensor may comprise, for example, a thermal sensor, an electrical sensor, a thermoelectric sensor, a microchip, a thermistor, a thermocouple and/or an ultrasonic sensor. Some embodiments may be configured such that they may be introduced to a surgical site through a minimally invasive introducer sheath. Optionally, the actuator allows a user to activate the jaw member and the ablation member with one hand.

Various embodiments of the devices and methods described briefly above are further described in the appended drawings and the following detailed description. The description of specific embodiments is provided for exemplary purposes and should not be interpreted to narrow the scope of the invention as defined in the claims.

BRIEF DESCRIPTION OF THE DRAWINGS

FIG. 7 is a perspective view of an elongate shaft ablation device, according to one embodiment of the invention.

FIG. 7a is a perspective view of the distal end of a shaft as in FIG. 6, with straight jaws, according to one embodiment of the invention.

DETAILED DESCRIPTION OF THE INVENTION

The present invention relates generally to medical devices and methods and more specifically to devices and methods for ablating cardiac tissue for treating cardiac arrhythmias such as atrial fibrillation. Ablation of cardiac tissue in various patterns has been shown to disrupt conduction pathways in the heart to ameliorate or eliminate AF or other arrhythmias. The devices and methods will often be used to ablate epicardial tissue in the vicinity of at least one pulmonary vein, but various embodiments may be used to ablate other cardiac tissues in other locations on a heart.

Generally, ablation devices of the invention include at least one tissue contacting member for contacting a portion of the epicardial tissue of a heart, securing means for securing the ablation device to the tissue and at least one ablation member coupled with the contacting member for ablating at least a portion of the tissue. In various embodiments, the devices have features which enable the device to attach to the epicardial surface with sufficient strength to allow the tissue to be stabilized via the device. For example, some embodiments may use suction force to secure the device to epicardial tissue and stabilize a beating heart to enable a beating heart ablation procedure. Other embodiments may include other optional features, such as sensors for sensing whether tissue has been ablated, a support member with an arm for connecting the device to a positioning device, cooling apparatus for cooling epicardial tissue, visualization devices and/or the like. Some embodiments of the device are introducible into a patient via minimally invasive means, such as a minimally invasive incision, sheath, trocar or the like.

Methods of the invention generally include contacting a device with epicardial tissue, using a tissue contacting member on the device to secure the device to the tissue, and ablating the tissue with an ablation member on the device. In some embodiments, the method further includes additional steps such as positioning the device on the epicardial tissue, stabilizing cardiac tissue, cooling cardiac tissue, positioning the device using a positioning device, visualizing epicardial tissue with an imaging device and/or the like. Again, although much of the following description focuses on embodiments used to treat AF by ablating epicardial tissue near one or more pulmonary veins on a human heart, the devices and methods may be used in veterinary or research contexts, to treat various heart conditions other than AF, to ablate cardiac tissue other than the epicardium and/or in any other suitable manner or context.

Figure 1:
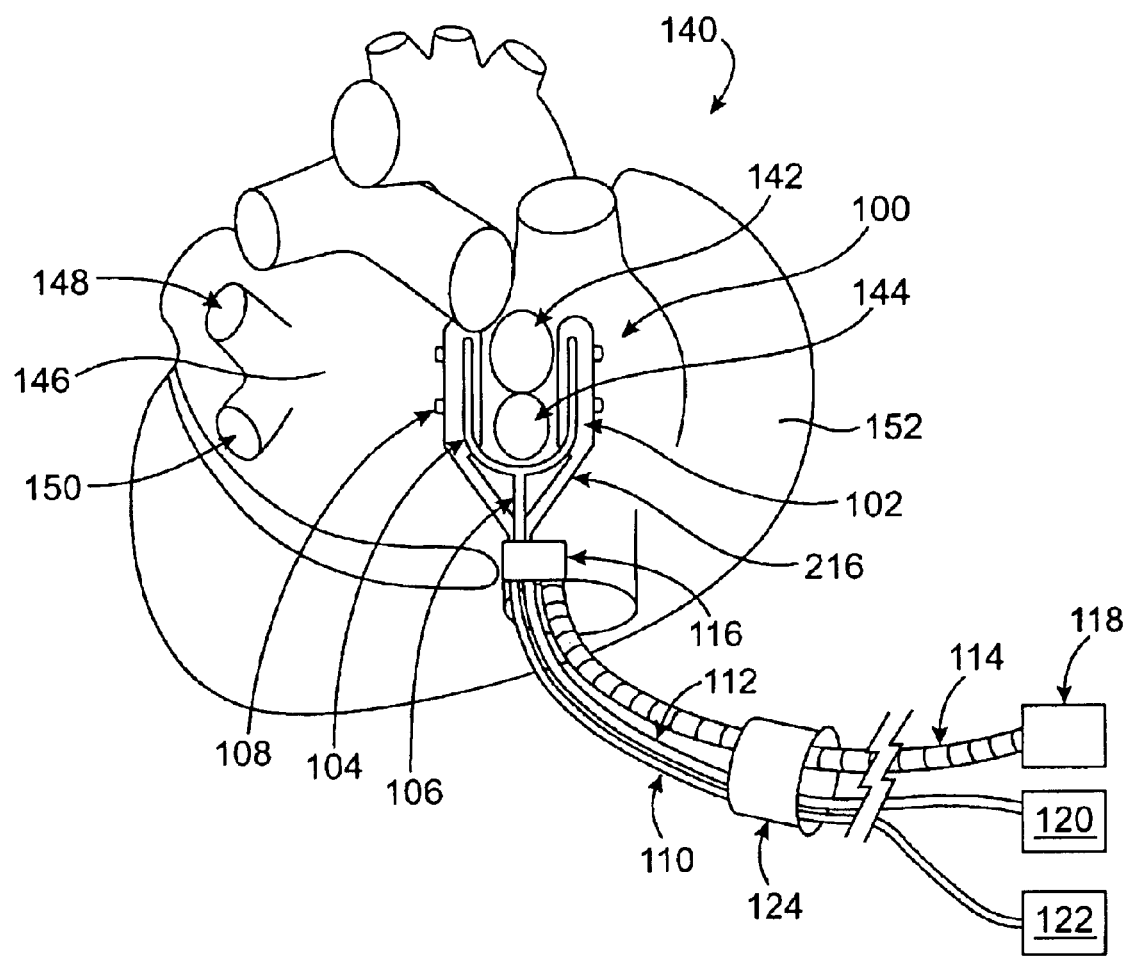
FIG. 1 is a perspective view illustration of a human heart and an ablation device in position for performing an ablation procedure, according to one embodiment of the invention.

Referring now to FIG. 1, an ablation device 100 is shown in position for ablating epicardial tissue on a human heart 140. A top view of ablation device 100 is shown, the visible components of device 100 including a tissue contacting member 102 coupled with a suction connector 216 and a support member 104 having a support arm 106. Tissue contacting member 102 also includes multiple artery securing arms 108 for securing one or more coronary arteries. Suction connector 216 is coupled with a suction cannula 112, which in turn is coupled with a suction source 120. Support arm 106 is coupled via a clamp 116 to a positioner 114, which in turn is coupled to a stabilizing device 118 for stabilizing positioner 114. Finally, an ablation member (not visible) of ablation device 100 is coupled, via a wire 110, to an energy source 122. In various embodiments, ablation device 100 may be introduced into a patient through a minimally invasive introducer device, such as a sheath 124, trocar or the like, as is represented in FIG. 1 by a simplified representation of sheath 124.

In FIG. 1, ablation device 100 is shown in a position partially encircling the right superior pulmonary vein 142 and the right inferior pulmonary vein 144. As will be described if further detail below, such a position is only one possible configuration for treating heart 140. In other embodiments, for example, both of the right pulmonary veins 142, 144 may be completely encircled, only one may be partially or completely encircled, the left superior 148 and/or left inferior 150 pulmonary veins may be partially or completely encircled and/or various patterns may be ablated on the left atrium 146, the right atrium 152 and/or the right and left ventricles (not labeled). Any ablation pattern suitable for heart treatment may be accomplished by one or more embodiments of the present invention. Thus, the following descriptions of various embodiments should not be interpreted to narrow the scope of the invention as set forth in the claims.

Generally, ablation device 100 includes at least one tissue contacting member 102 coupled with at least one ablation member (not shown in FIG. 1). One embodiment of a device which may be used as tissue contacting member 102 is described in U.S. patent application Ser. No. 60/182,048, filed on Feb. 11, 2000, the entire contents of which is hereby incorporated by reference. Ablation device 100 shown in FIG. 1 actually includes two tissue contacting members 102, one on either side of the right pulmonary veins 142, 144. Tissue contacting members 102 may be coupled together via support member 104 and suction connector 216. In other embodiments, some of which will be described below, tissue contacting member 102 may include only one member, more than two members, a coupling member disposed between multiple arms and/or the like. Alternatively, tissue contacting member 102 may be conical, linear, shaped as a flat pad or a flat elongate member or may have any other suitable configuration. Additionally, tissue contacting members 102 may have any suitable size and dimensions. For example, in FIG. 1, tissue contacting members 102 and device 100 in general have a shape and dimensions to contact and ablate epicardial tissue on heart 140 in a pattern partial encircling the right pulmonary veins 142, 144. Many other configurations and sizes are possible, as described further below.

Tissue contacting members 102 may be manufactured from any suitable material, such as a polymer, plastic, ceramic, a combination of materials or the like. In one embodiment, for example, tissue contacting members 102 are manufactured from a liquid molded silicone rubber. In some embodiments, the material used to make tissue contacting members 102 is chosen to allow the members 102 to be at least partially deformable or malleable. Deformable tissue contacting members 102 may allow ablation device 100 to be inserted into a patient and/or advanced to a surgical site within the patient via a minimally invasive incision or a minimally invasive introducer device, such as sheath 124. Deformable tissue contacting members 102 may also allow device 100 to conform to a surface of heart 140, to enhance ablation of epicardial or other cardiac tissue. In some embodiments, tissue contacting members 102 include one or more artery securing arms 108, for securing, exposing and/or occluding one or more coronary arteries via silastic tubing attached between the artery and securing arm 108. Securing arms 108 are generally made of the same material (s) as tissue contacting members 102 but may also suitably comprise other materials.

In some embodiments, tissue contacting members 102 are coupled with support member 104. Support member 104 may be made of any suitable biocompatible material, such as titanium, stainless steel, nickel titanium alloy (Nitinol) or the like. Support member 104 may be coupled with tissue contacting members 102 by any suitable means, such as but not limited to one or more adhesive substances, placement of a portion of support member 104 within a sleeve on tissue contacting members 102 or a combination of both. Like tissue contacting members 102, support member 104 may also be malleable or deformable to allow for insertion of ablation device 100 through a minimally invasive sheath 124 and/or for enhancing conformability of device 100 to a surface of heart 140. Support member 104 typically includes at least one support arm 106 or similar protrusion or multiple protrusions for removably coupling ablation device 100 with positioner 114 or one or more other positioning devices. Positioner 114, for example, may comprise a flexible, positioning arm, with attachment means such as clamp 116 for attaching to support arm 106 and stabilizing device 118 for stabilizing positioner 114. For example, a flexible, articulating positioner 114 may be of the type which rigidities when tensile force is applied, such as via a tensioning wire. Any other suitable positioner 114 may alternatively be used. In other embodiments, device 100 may not include support member 104. Such devices 100 may incorporate a connection arm onto a tissue contacting member 102, may be positioned on heart 140 using a positioning device inserted through a separate incision, or may be positioned or manipulated by a physician or other user via any other suitable means.

Tissue contacting members 102 may also be coupled with one or more suction cannulas 112 to provide suction for enhancing contact of ablation device 100 with epicardial tissue. In various embodiments, tissue contacting members 102 may be directly coupled to one or more cannulas 112 or may be connected via one or more suction connectors 216. In FIG. 1, a V-shaped suction connector is used to couple the two tissue contacting members 102 with a common cannula 112. Cannula 112, in turn, is connected to suction source 120, which may be a conventional wall suction or stand-alone suction source. Generally, cannula 112 may be any suitable conventional cannula 112, which are well known to those skilled in the art. Suction connector 216 is typically comprised of the same material(s) as tissue contacting members 102, but may also be made of a material or materials used to make cannula 112. Suction connector 216 may further include a nozzle 218 (FIG. 2) for connecting to cannula 112.

Figure 2:
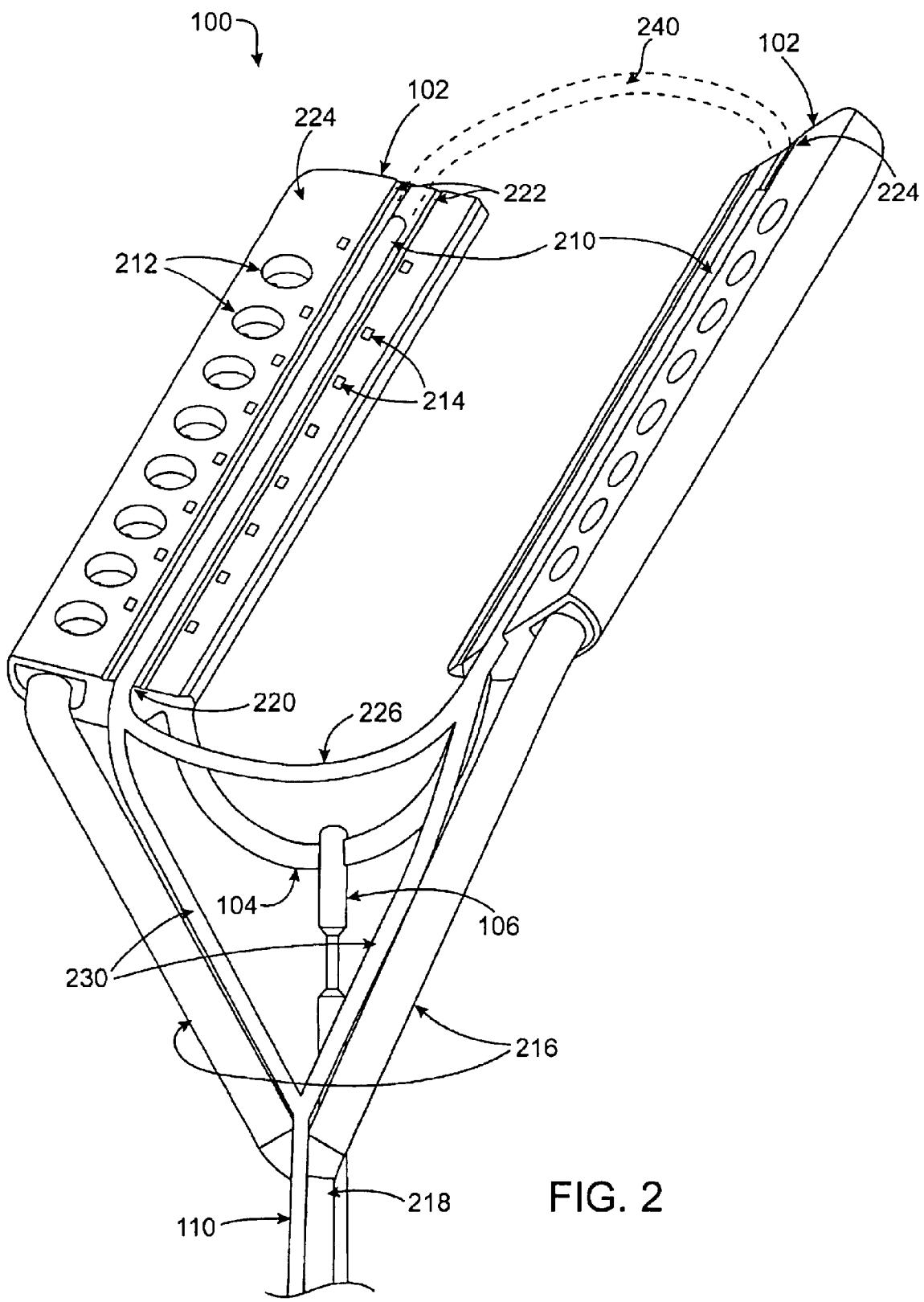
FIG. 2 is a perspective view of an ablation device, according to one embodiment of the invention.

Ablation device 100 also includes at least one ablation member 210 (FIG. 2). Ablation member 210 typically receives energy from a separate energy source 122, although ablation members 210 with internal energy sources are also contemplated. Where a separate energy source 122 is used, ablation member 210 may be coupled with source 122 by any suitable means. In one embodiment, for example, ablation member 210 may be coupled to energy source 122 with wire 110. Wire 110 may be any suitable connector, such as fiber optic cable, electric cable, coaxial cable, ultrasound transmission device or the like. As is described further below, any suitable energy may be provided by energy source 122 for ablation and any means for transmitting energy to ablation member 210 is contemplated within the scope of the invention. In some embodiments, for example, energy may be transmitted remotely, so that no wires or other similar connecting devices are required. In other embodiments, radio frequency energy may be provided by an RF energy source and transmitted to ablation member 210 via conventional electrical wire(s) 110.

Generally, ablation member 210 may be configured to transmit energy of any suitable quantity or force. For example, in some embodiments sufficient energy will be transmitted through ablation member 210 to ablate only epicardial tissue on a heart. In other embodiments, sufficient energy may be transmitted to cause one or more layers beneath the epicardial tissue to be ablated. In some embodiments, for example, one or more transmural lesions (across the entire wall of the heart) may be ablated. Typically, an amount of energy transmitted through ablation member 210 will be adjustable to create an desired ablation depth.

As mentioned briefly above, a minimally invasive introducer sheath 124, trocar or other minimally invasive device may be used for introducing one or more of the components shown in FIG. 1 into a patient. In some embodiments, a sheath need not be used and instead only a minimally invasive incision is used. In other embodiments, multiple minimally invasive incisions and/or sheaths 124 may be used for introducing various devices into a patient. For example, one sheath 124 may be used for introducing ablation device 100 and another sheath 124 may be used for introducing positioner 114. Although devices and methods of the present invention are often suitable for minimally invasive procedures, they may also typically be used in open surgical procedures, either with or without cardiopulmonary bypass, in various embodiments.

Referring now to FIG. 2, an embodiment of ablation device 100 is shown in further detail. Device 100 is shown from a bottom/angled view to show a tissue contacting surfaces 224 of tissue contacting members 102, ablation member 210, suction apertures 212 and sensors 214. Like tissue contacting members 102, tissue contacting surfaces 224 may be given any configuration and sizes to contact cardiac tissue in an area around the tissue to be ablated. For example, in an embodiment as in FIG. 2 a tissue contacting surface 224 on one tissue contacting member 102 may have a length of approximately 1.25 in. and a width of approximately 0.5 in., with a space between the two tissue contacting surfaces measuring approximately 0.4 in. Such exemplary dimensions are in no way limiting, and all combinations of dimensions for one or more tissue contacting members 102 are contemplated. In some embodiments, as in FIG. 2, surfaces 224 may be flat and smooth. In other embodiments, surfaces 224 are textured, curvilinear or otherwise shaped to enhance contact of tissue contacting members 102 with heart 140. Some embodiments may further include one or more surface features 222. Such features 222 may enhance friction between tissue contacting surfaces 224 and epicardial tissue and/or may provide an area for placement of additional features, such as irrigation apertures for cooling tissue or the like.

Ablation member 210 may include one or more ablation members for transmitting one or more of a variety of ablation agents to epicardium or other cardiac tissue. In some embodiments, as commonly shown in the drawing figures, ablation member 210 may comprise a single, continuous, RF ablation coil or wire for transmitting RF energy to cardiac tissue. In other embodiments, ablation member 210 may be multiple radio frequency devices or one or more cryogenic devices, ultrasound devices, laser devices, thermo-electric chip devices, chemical agent delivery devices, biological agent delivery devices, light-activated agent devices, thermal devices, microwave devices, or ablating drug delivery devices. Other suitable ablation devices are also contemplated within the scope of the invention. Additionally, radio frequency ablation members 210 may be bipolar or unipolar in various embodiments. In conjunction with any of these various embodiments, energy source 122 may provide any of the above-listed types of ablative energy or substance, any combination thereof or any other suitable ablative energy or substance.

Ablation member 210 may be given any configuration or size for ablating cardiac tissue. In the embodiment shown in FIG. 2, for example, ablation member 210 has two linear portions disposed along most of the lengths of contacting surfaces 224 of tissue contacting members 102, and the linear portions are continuous with a curved portion 226 so that ablation member 210 is generally U-shaped. Alternatively or additionally, ablation member 210 may continue proximally from tissue contacting members 102 in one or more arms 230 which eventually connect to wire 110 or other connective device. In some embodiments, curved portion 226 may be eliminated so that ablation member 210 comprises two linear ablation members connected to wire 110 via arms 230. In yet other embodiments, arms 230 may be eliminated and ablation member 210 may be coupled directly to wire 110 without interposing arms.

Generally, ablation members 210 and tissue contacting member 102 may have any shapes, sizes, configurations or combinations of shapes and sizes to produce a desired ablation pattern on epicardial or other tissue of a heart. In some examples, ablation members 210 and tissue contacting members 102 are configured to partially or completely encircle or surround one pulmonary vein. In other embodiments, they may be configured to partially or completely surround two pulmonary veins on the same side of the heart, such as the left superior and left inferior pulmonary veins. In still other embodiments, the right and left inferior pulmonary veins or the right and left superior pulmonary veins may be partially or wholly encircled. And in still other embodiments, all four pulmonary veins may be partially or completely encircled by ablation members 210 and tissue contacting member 102. Some of these embodiments are described in further detail below, but it should be understood that any possible configuration is contemplated within the scope of the present invention.

In some embodiments, all or a portion of ablation member 210 or tissue contacting member 102 may be steerable. Steerability means that an ablation member 210 or tissue contacting member 102 may be adjusted to fit around or next to one or more pulmonary veins or to otherwise assume a desired configuration. For example, some embodiments may include a pull wire coupled with ablation member 210 and/or tissue contacting member 102. The pull wire, when pulled, deflects ablation member 210 and/or tissue contacting member 102 to one side or around a curved structure. Other embodiments may include pushable wires, combinations of flexible and stiff portion and/or the like to provide steerability.

In some embodiments, for example, it is desirable to ablate epicardial tissue in a circumferential pattern around one or more pulmonary arteries. Various configurations of tissue contacting members 102 and ablation members 210 are contemplated for achieving such ablation patterns. For example, a retractable RF coil 240 or other retractable ablation device may be incorporated into or used in conjunction with ablation member 210 as shown in FIG. 2. Retractable coil 240 could be housed within tissue contacting member 102, for example, and could be released when desired to surround or encircled one or two pulmonary veins. As already described, the RF ablation member 210 and/or the RF retractable coil 240 pictured in FIG. 2 may be replaced, in other embodiments, with devices using radio frequency energy, ultrasound energy, microwave energy, cryogenic energy, thermoelectric energy or laser energy for ablating tissue. For example, ablation member 210 in some embodiments comprises multiple thermoelectric chips disposed in a pattern on tissue contacting members 102.

Although ablation device 100 and ablation member 210 are often shown as being generally U-shaped, many other configurations are possible. As described further below, a ablation device 100 may be conical in shape, with ablation member 210 being disposed in a circle at the base of the cone which contacts cardiac tissue. In other embodiments, device 100 may be configured as a flat patch and one or more linear or curvilinear ablation members 210 may be incorporated into the patch. For example, ablation device 100 may include a combination of multiple ablation members 210 to ablate a pattern on heart 140 such as: a first linear ablation member for contacting heart tissue between a left pulmonary vein and a right pulmonary vein; a second linear ablation member for contacting heart tissue at a location approximating a line extending to the atrioventricular groove; and a third linear ablation member for contacting heart tissue on a left atrial appendage. In such an embodiments, one or more of ablation members 210 may overlap one another. In some embodiments involving multiple ablation members 210, each member may be controllable on a separate radio frequency channel or other energy transmission channel.

Tissue contacting members 102 optionally include one or more attachment means for enhancing contact of ablation device 100 with epicardial or other cardiac tissue. In some embodiments, one or more suction apertures 212 are used. Each suction aperture 212 generally includes a depressed surface and a small suction hole. The suction hole is connected to a lumen (not shown) within tissue contacting member 102, and the lumen is then couplable with a suction cannula 122 or connector 216 for connecting to cannula 122. Suction apertures 212 may be given any suitable configuration, size or pattern. For example, suction holes may be disposed on tissue contacting member 102 is a largely linear pattern, as in FIG. 2. In other embodiments, suction apertures may be arranged in two parallel lines such that ablation member 210 is disposed between the two parallel lines of suction apertures 212. In still another embodiment, ablation device 100 may include one tissue contacting member 102 having a conical shape, with the base of the cone contacting epicardial tissue and the entire conical tissue contacting member 102 acting as one suction aperture.

In some embodiments, suction force may be applied via suction apertures 210 with sufficient strength to allow for stabilization and/or positioning of heart 140. For example, a physician may place ablation device 100 on a beating heart 140, apply suction, and hold heart 140 is a relatively stable or reduced-motion position while performing an ablation procedure. The physician may also (or alternatively) turn or otherwise move heart 140, using ablation device 100, such as when a different angle of heart 140 would be advantageous for viewing or treating a portion of heart 140. In these or other embodiments, suction force applied through suction apertures 212 may be of sufficient strength to dissect through one or more layers of adipose tissue covering epicardial tissue. Such dissection by suction apertures 212 may allow for improved contact of the epicardial tissue by device and, thus, improved ablation. In alternative embodiments, suction apertures 212 may be replaced or supplemented by other means for securing ablation device 100 to epicardial tissue. For example, an adhesive may be applied to tissue contacting surfaces 224. Such adhesives or other securing means may also be sufficiently strong, in some embodiments, to allow for positioning and/or stabilization of heart 140.

Tissue contacting members 102 may also include one or more sensors 214 for sensing when tissue has been ablated. Sensors 214 may include one or more thermal sensors, electrical sensors, thermoelectric sensors, microchips, thermistors, thermocouples and ultrasonic sensors. As shown in FIG. 2, some embodiments include two or more paired sensors 214, with one sensor of each pair on one side of ablation member 210 and the other sensor on the opposite side. In some embodiments, one sensor 214 transmits a signal through epicardial tissue to its paired sensor 214. If epicardial tissue between the two paired sensors 214 has been ablated, then energy will transmit poorly through that ablated tissue. Thus, the receiving sensor 214 will receive reduced or no energy transmitted from the transmitting sensor 214. If tissue between two paired sensors has not been ablated, the signal should travel through the tissue with only slight reduction in strength. By using such paired sensors 214 and comparing signals received in different pairs, areas of ablation can be compared, to determine if all desired areas for ablation have been sufficiently ablated. Other configurations one or more sensors 214 may also be used.

Figure 2A:
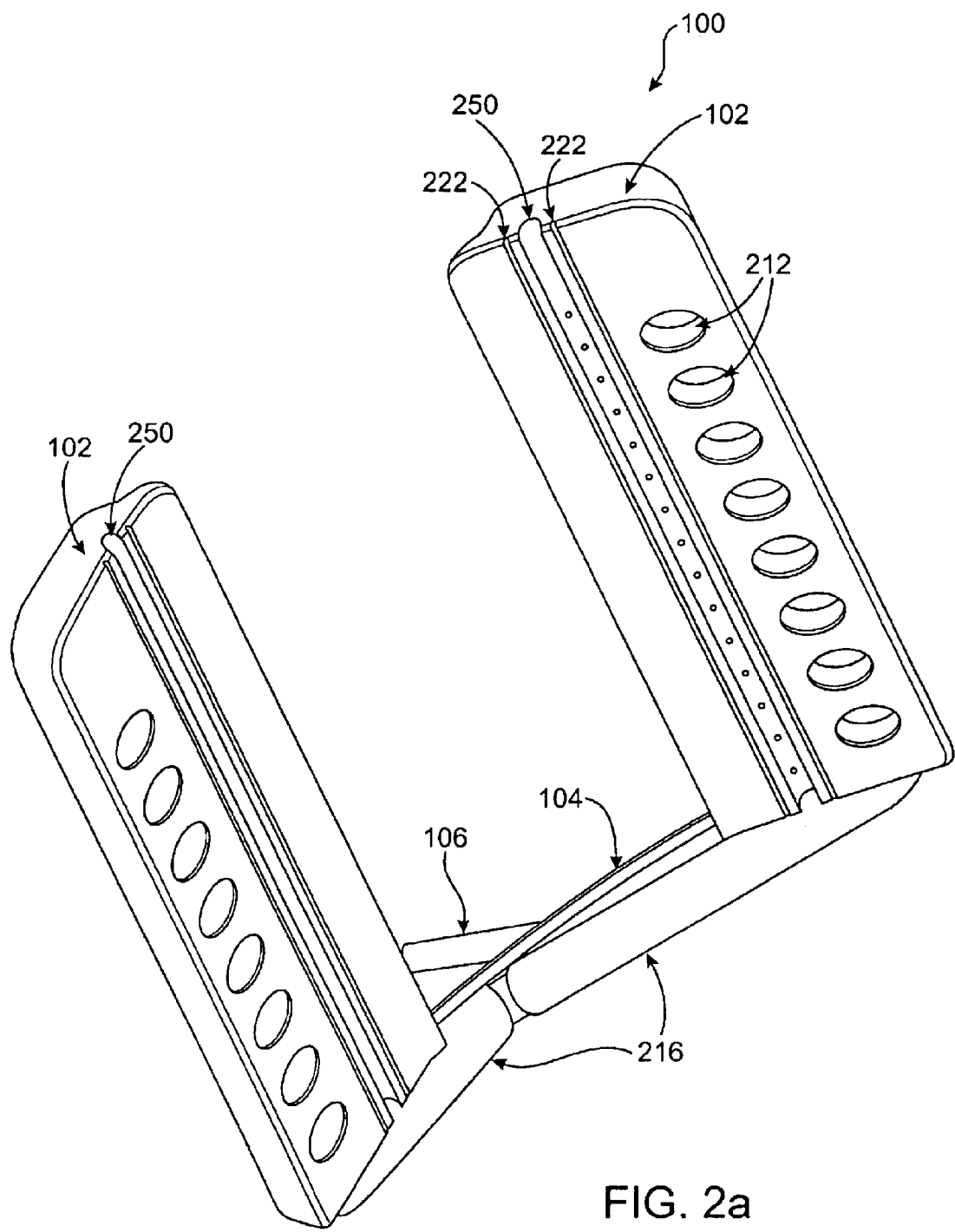
FIG. 2a is a perspective view of the ablation device shown in FIG. 2, with the ablation member removed.

Referring now to FIG. 2*a*, another view of ablation device 100 as in FIG. 2 is shown, with ablation member 210 removed for clarity. In some embodiments, tissue contacting members 102 include a linear trough 250 in which ablation member 210 is placed, either removably or permanently.

Positioning ablation member 210 in trough 250 may provide improved contact between ablation member 210 and epicardial tissue while also providing ablation device 100 with durability. Surface features 222 are again shown in FIG. 2a. These features may simply enhance contact of tissue contacting members 102 with epicardial tissue or may also contain additional features, such as sensors, irrigation apertures for allowing passage of irrigation fluid for cooling ablated tissue, small suction apertures and/or the like.

Optionally, various embodiments of ablation device 100 may further include at least one cooling member for cooling a portion of ablated epicardial tissue, epicardial tissue surrounding an ablated area, other nearby tissues and/or a portion of device 100. Cooling members are not shown in the drawing figures, for purposes of clarity. Generally, a cooling member may comprise any suitable device for cooling a tissue. In some embodiments, cooling member includes at least one inlet port, for allowing introduction of a cooling substance into the member, a hollow internal cooling member, and at least one outlet port for allowing egress of the cooling substance. The cooling substance itself may be carbon dioxide, any other suitable gas, saline or any other suitable liquid. In some embodiments, the hollow cooling member comprises a tubular member disposed within tissue contacting member 102 in general proximity with ablation member 210. In other embodiments, cooling member may comprise a chamber for containing cooling substance or a series of irrigation holes for allowing cooling substance to flow out of tissue contacting member 102 to contact ablated or other epicardial tissue. Many other suitable cooling apparatus are contemplated for use within the scope of the present invention.

Figure 3:
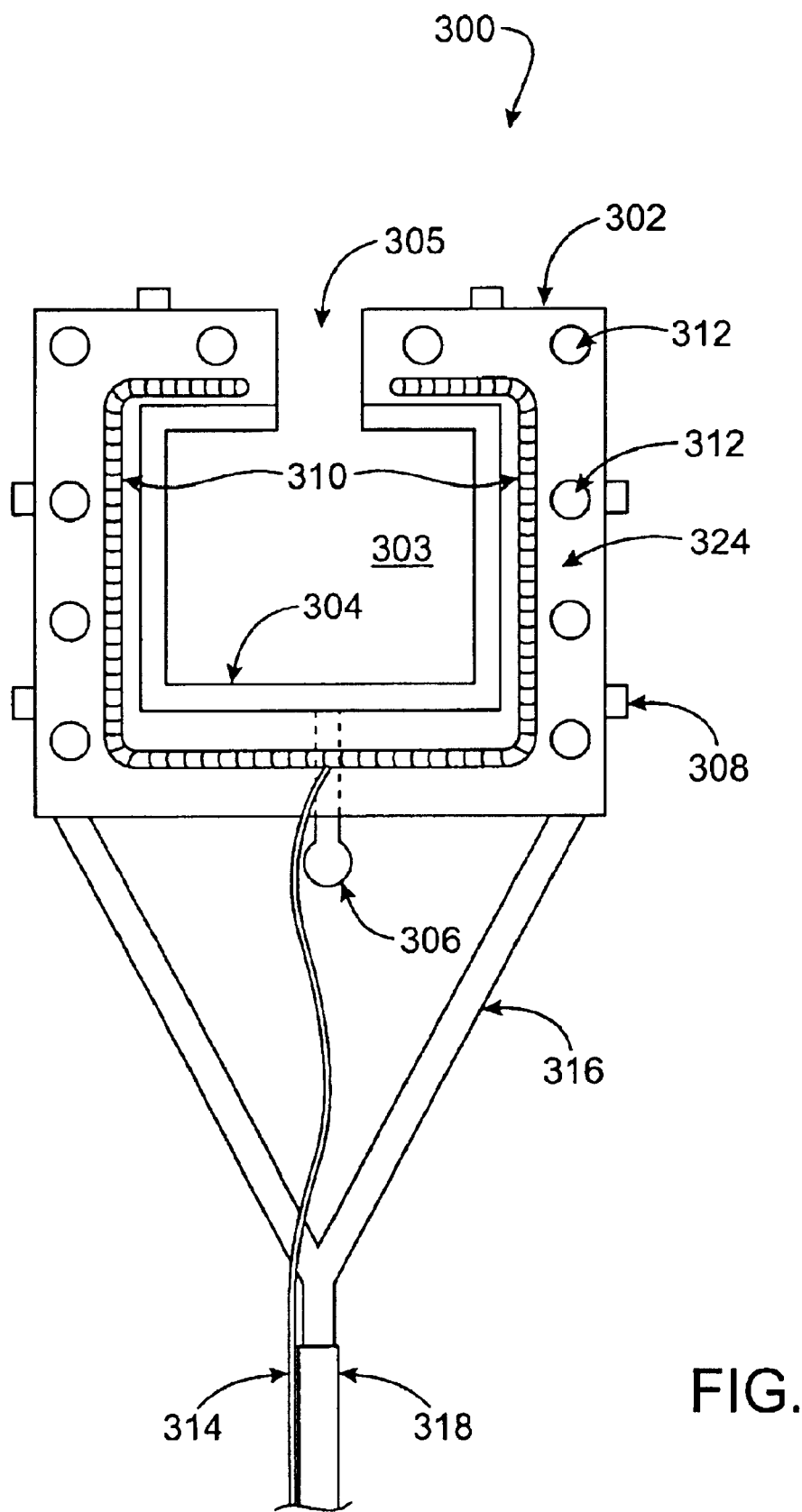
FIG. 3 is a bottom-surface view of an ablation device, according to one embodiment of the invention.

With reference now to FIG. 3, another embodiment of ablation device 300 is shown from a bottom-side view. Ablation device 300 includes a tissue contacting member 302, coupled with an ablation member 310 and a support member 304. As with some above-described embodiments, tissue contacting member includes a tissue contacting surface 324, tissue attaching means including multiple suction apertures 312 and multiple artery securing arms 308. Tissue contacting member 302 is removably couplable with a suction cannula 318 via a V-shaped suction connector 316. Ablation member 310 is coupled with energy transmitting wire 314 for coupling with an energy source (not shown). Support member 304 includes a support arm 306 (shown partially in dotted lines, since it extends on the opposite side of tissue contacting member 302) for coupling device 300 with a positioning device.

In ablation device 300, tissue contacting member 302, ablation member 310 and support member 304 are all generally shaped as a square with a central area 303 and a top area 305 left open. Such a configuration may be used, for example, to contact and ablate epicardial tissue almost completely encircling one or more pulmonary veins. Leaving top area 305 open may allow device 300 to be positioned around such veins or other vessels while still providing almost circumferential ablation. In other embodiments, either central area 303, top area 305 or both may be closed to provide for different contact and/or ablation patterns on epicardial tissue. In still other embodiments, one or more hinges may be positioned on ablation device 300 to allow top area 305 to be closed after positioning device 300 around one or two pulmonary veins. Again, any configuration, shape, size, dimensions or the like are contemplated within the scope of the invention.

Figure 4:
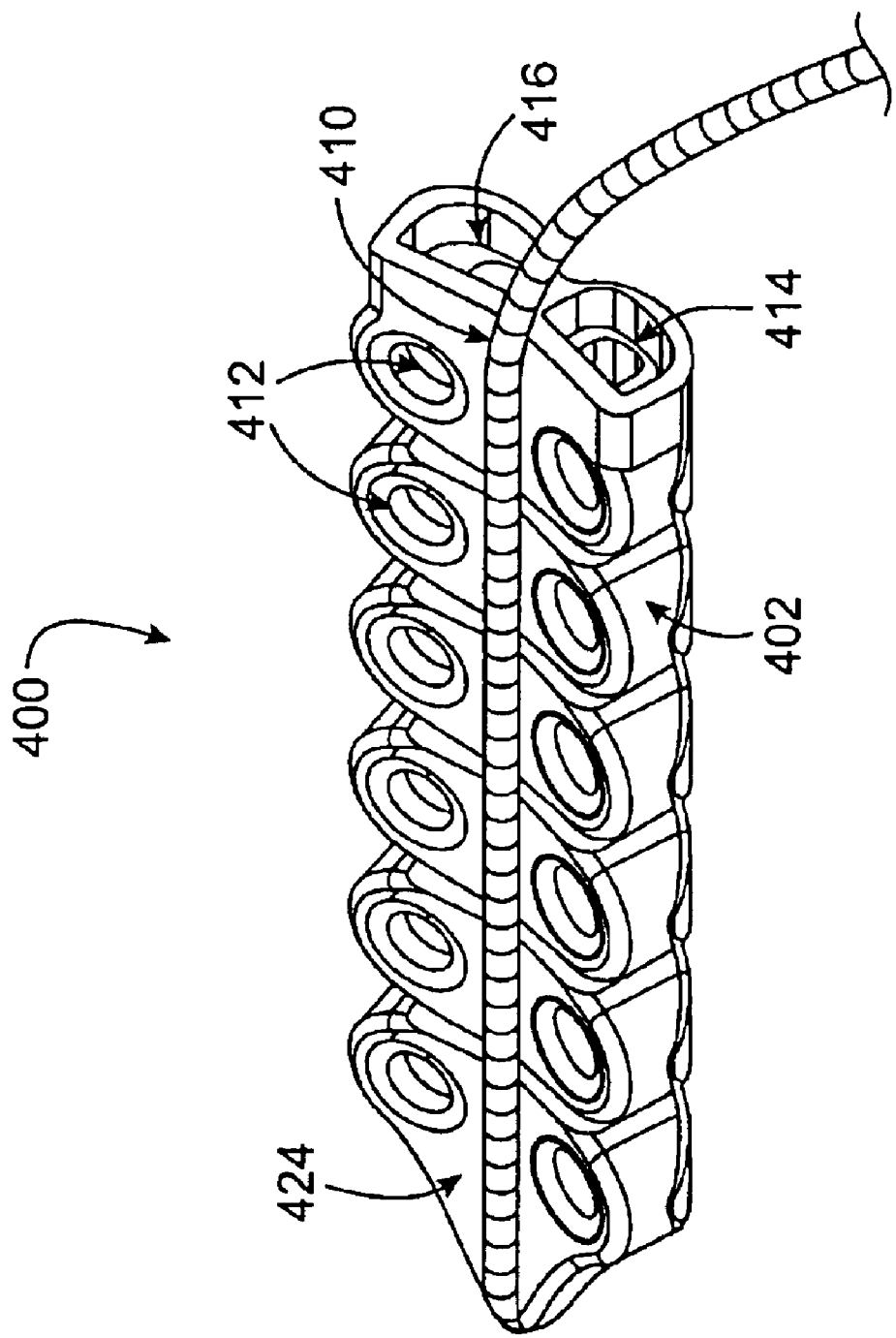
FIG. 4 is a perspective view of a flexible, elongate ablation device with two rows of suction apertures, according to one embodiment of the invention.

Referring now to FIG. 4, another embodiment of ablation device 400 comprises a largely flexible device which includes a tissue contacting member 402 and an ablation member 410. Tissue contacting member 402 may be made of any suitable, flexible material, such as a silicone, polyurethane, polycarbonate, another suitable polymer or combination of polymers or the like. Tissue contacting member 402 generally includes a tissue contacting surface 424 having multiple suction apertures 412. Tissue contacting surface 424 may be slightly concave (as shown), flat or may have any other suitable shape. Suction apertures 412 are disposed in two parallel lines, one line on either side of ablation member 410 and communicate with suction lumens 414 and 416. Suction lumens 414, 416 may be coupled with one or more suction cannulas or similar devices for providing suction force through suction apertures 412. Other embodiments may include one common suction lumen for connection to a suction cannula.

As with various embodiments described above, any suitable ablation means may be used as ablation member 410 in device 400. In the embodiment shown, ablation member 410 comprises a linear radio frequency coil. Ablation member 410 may extend beyond the length of tissue contacting member 402, either in a proximal or distal direction and may be coupled with a source of energy via a wire (not shown) or other connection device. In various embodiments, one or more of the features described above, such as support members, retractable ablation elements, sensors, cooling members, positioning arms and/or the like may be incorporated into or used with ablation device 400. Alternatively, ablation device 400 may simply include tissue contacting member 402 and linear ablation member 410. Such an embodiment may be advantageous for introduction through a narrow, minimally invasive introducer sheath, due to the device's flexibility and relatively small size. In one embodiment, for example, device 400 may measure approximately 3.25 in. in length and approximately 0.9 in. wide and may further be deformable to a narrower configuration for insertion through a sheath. Furthermore, device 400 may be sufficiently flexible to conform to curved surfaces of heart 140, allowing for enhanced contact with and ablation of epicardial tissue. Finally, it may sometimes be advantageous to ablate epicardial tissue in a linear pattern or in multiple line. Ablation device 400 may be movable, to allow ablation in a first line, a second line, a third line and/or the like.

Figure 4A:
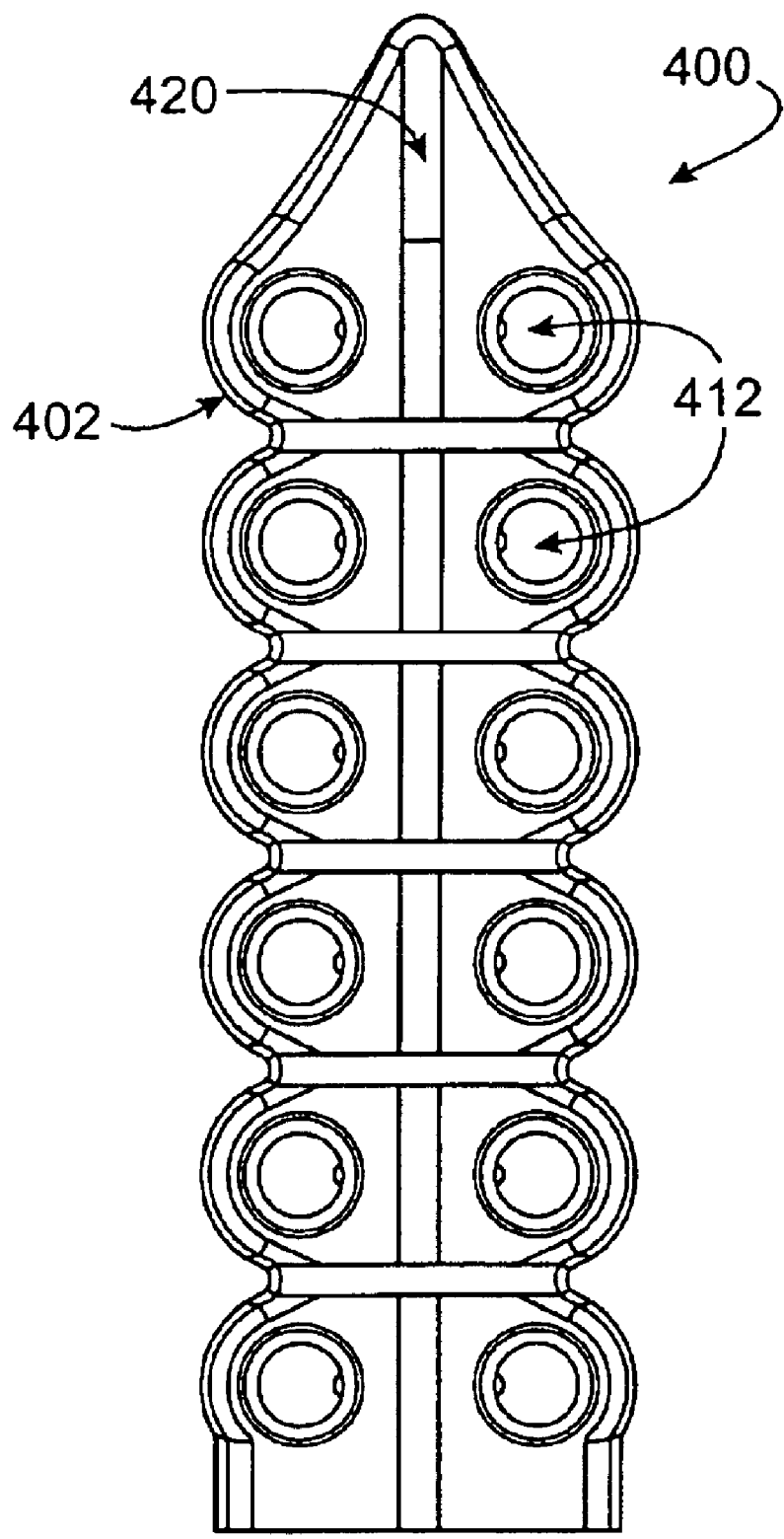
FIG. 4a is a bottom-surface view of the ablation device as shown in FIG. 4, with the ablation member removed.

Referring now to FIG. 4a, a bottom-side view of ablation device 400 is shown with ablation member removed. It can be seen that tissue contacting member 402 may include a trough 420 in which ablation member 410 may be positioned. In some embodiments, ablation member 410 may be a removable piece which may be removably attached to tissue contacting member 402, at least partially disposed within trough 420, so that one ablation member 410 may be used with multiple tissue contacting members 402, one after another, for example if tissue contacting members 402 are single-use, disposable devices.

Figure 5:
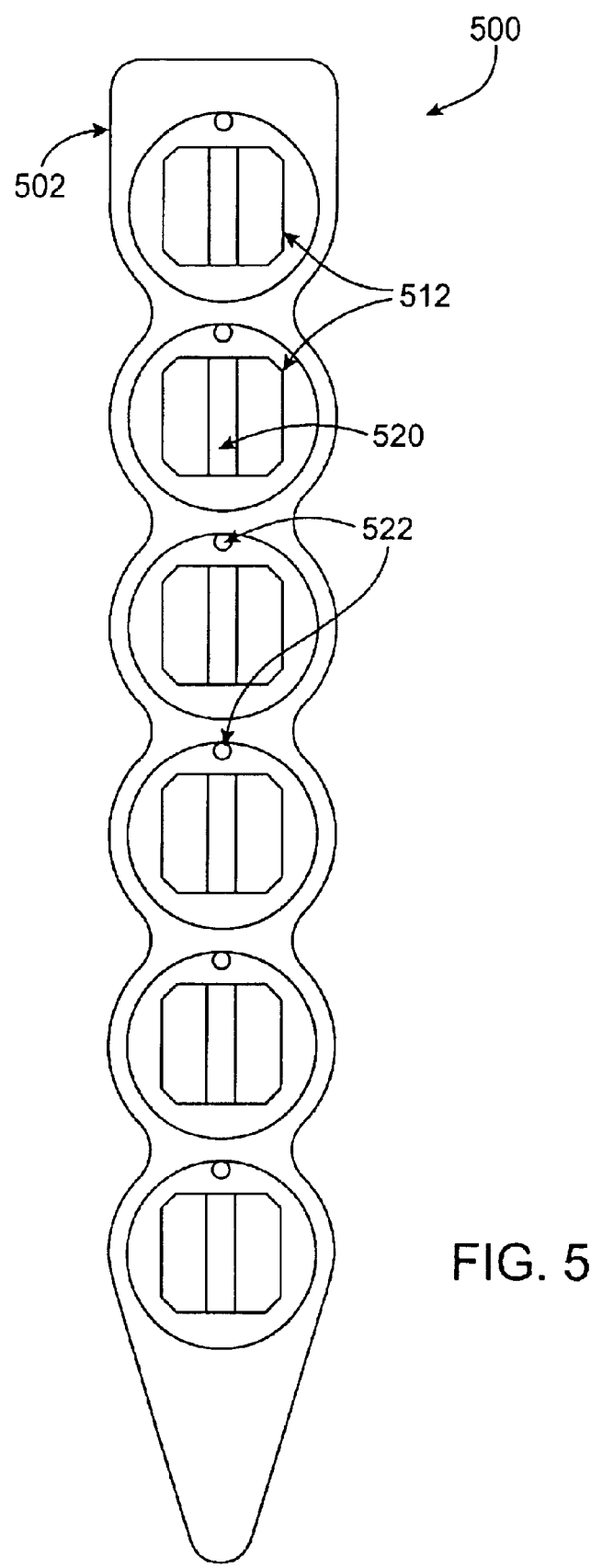
FIG. 5 is a bottom-side view of a flexible, elongate ablation device with one row of suction apertures, according to one embodiment of the invention.

FIG. 5 shows yet another embodiment of ablation device 500, including a tissue contacting member without an ablation member being shown. Device 500 is similar to ablation device 400, but tissue contacting member 502 has one row of suction apertures 512 rather than two and ablation member, placed in ablation trough 520, overlays suction apertures 512. Suction holes 522 shown in suction apertures 512 demonstrate that the apertures sometimes include both a depressed or concave surface and one or more holes communicating with a suction lumen. The embodiment of ablation device 500 in FIG. 5 may be advantageous for forming one or more linear ablations on heart 140 when there is minimal space in which to manipulate device 500 and/or when a narrow, minimally invasive incision or sheath is desired for insertion of device 500. Device 500 may be manufactured from any suitable material or combination of materials, such as those described above, may use any suitable form of ablation member and may include various additional features as desired.

Figure 6:
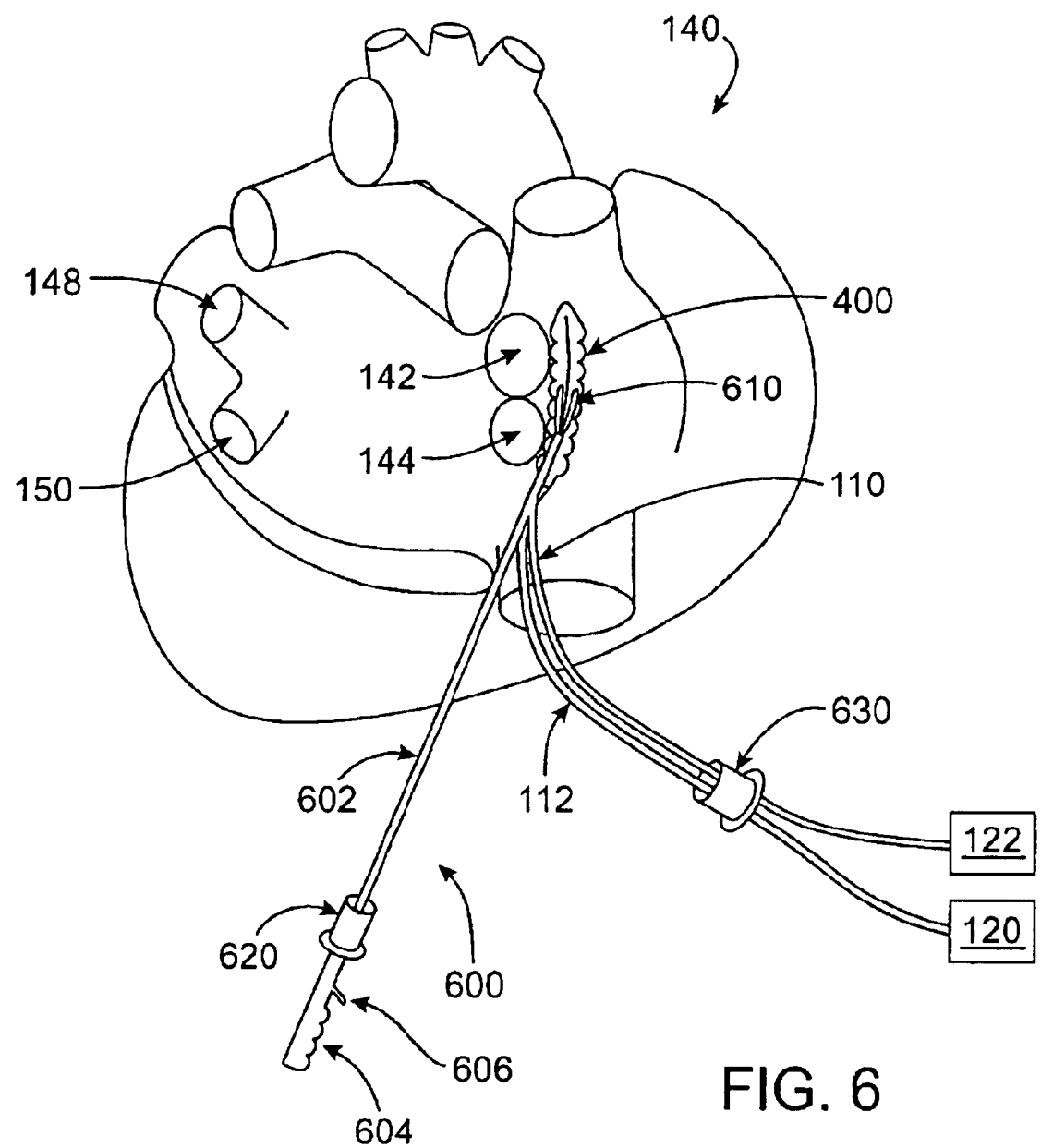
FIG. 6 is a perspective view of a human heart and an ablation device in position for performing an ablation procedure, according to one embodiment of the invention.

Referring now to FIG. 6, ablation device as described with reference to FIGS. 4 and 4a is shown in position for performing epicardial ablation on a human heart 140. Generally, ablation device 400 may be placed in any desired position on heart 140 for ablating epicardial tissue. Thus, in various embodiments device may be placed adjacent one or both of the right pulmonary veins 142, 144, adjacent one or both of the left pulmonary veins 148, 150, or in any other suitable location. Furthermore, ablation device 400 may be used to ablate tissue in a linear pattern at one location and then may be moved to ablated tissue in a linear pattern in another location. As discussed above with reference to various embodiments, ablation device 400 may be introduced into a patient via a minimally invasive device, such as a sheath 630 or trocar, and may be coupled with a source of suction 120 via a suction cannula 112 and with a source of ablative energy 122 via a wire 110 or other connective device.

Ablative device 400, as well as other embodiments of ablative devices described above, may be positioned on heart 140 via a positioning device 602 which is introduced via a second minimally invasive incision or second sheath 620. Second sheath 620 may be placed at any suitable location on the patient to allow access to ablation device with the positioning device 602. Positioning device 602 may then be introduced through sheath and advanced to the position of ablation device 400. Positioning device 602 may then be used to secure device 400, such as by opposable jaws 610 or any other suitable means, and position device 400 in a desired location on heart 140. In some embodiments, positioning device may further be used to reposition device 400 to perform ablation in multiple locations on heart 140. The proximal end of positioning device 602 may include a handle 604 for holding and manipulating device 602 and one or more actuators 606, such as a trigger for opening and closing opposable jaws 610 or other distally positioned end effectors of device 602. Examples of positioning device 602 may include, but are not limited to, conventional minimally invasive surgical devices such as laproscopic surgical devices and the like.

Referring now to FIG. 7, another embodiment of ablation device 700 suitably includes at least one elongate shaft 702 having a proximal end 724 and a distal end 726, a jaw member 704 coupled with shaft 702 near distal end 726, at least one ablation member 712, 714 coupled with jaw member 704, and a handle 706 and at least one actuator 708, 710 near the proximal end 724 for manipulating device 700, opening and closing the jaw member, activating ablation member 712, 714 and the like. Device 700 is generally configured to be introduced through a minimally invasive sheath, trocar or incision, though it may also be used in open surgical procedures. Shaft 702 may be made of any suitable material, such as metal, ceramic, polymers or any combination thereof, and may be rigid along its entire length or rigid in parts and flexible in one or more parts. In various embodiments, the shaft may be malleable, may articulate about at least one joint and/or may be steerable for positioning the device. In some embodiments, the ablation member is coupled with a portion of the shaft.

Jaw member 704 may be disposed on or near distal end 726 of shaft 702 and is generally configured to open and close to grasp epicardial or other tissue between the opposing jaws. For example, jaw member 704 may be coupled with shaft 702 at a hinge point 730 to allow for such opening and closing motion. An ablation member is coupled with at least part of jaw member 704. As with the above-described embodiments, the ablation member may use any suitable energy source for ablating tissue. In some embodiments, multiple ablation members 712, 714 may be used. For example, one electrode 712 of a bipolar ablation member may be coupled with one opposing jaw and another electrode 714 may be coupled with the other opposing jaw. Alternatively, ablation members 712, 714 may include one unipolar ablation device or any of the ablation devices described with reference to various embodiments above. The jaw member and/or the ablation member may be shaped to contact and ablate the epicardial tissue in a pattern such as, but not limited to, a U-shaped pattern, an L-shaped pattern, a circular pattern or a linear pattern. Actuators 708, 710 may have one or more various functions, such as opening and closing jaw member 704, activating ablation members 712, 714, changing an angle of orientation of jaw member 704, straightening or bending jaw member 704 and/or the like. One actuator 710, for example, may comprise a trigger-like actuator while another actuator 708 may comprise a turnable dial.

Generally, jaw member 704 may have any suitable configuration for contacting a surface of a heart, for grasping epicardial or other tissue to be ablated and/or for placing ablation members 712, 714 in contact with tissue to be ablated. As such, jaw members 714 may be straight, curved, bent or otherwise configured for contacting, grasping and/or ablating tissue. In some embodiments, jaw member 704 may be adjustable via an actuator 708, 710, so as to allow their shapes to be bent, straightened or the like during a procedure. With reference to FIG. 7a, one embodiment of a straight jaw member 718 may allow jaw member 718 to be retracted within shaft (arrows). Retraction may help protect a patient as well as jaw member during insertion and advancement of the device within the patient. Again, ablation members 720, 722 on such straight jaw members 718 may be bipolar RF members, unipolar RF members or any other suitable ablation devices.

Optionally, the device may further include an insulation member at least partially surrounding the device to protect body structures in the vicinity of the epicardial tissue to be ablated from damage due to heat or electrical current. Also optionally, the ablation member may be adjustable to deliver two or more varying amounts of ablative energy to two or more locations on the epicardial tissue. Various embodiments may further include at least one sensor for sensing a quantity of ablation provided by the ablation member to the tissue.

Figure 8:
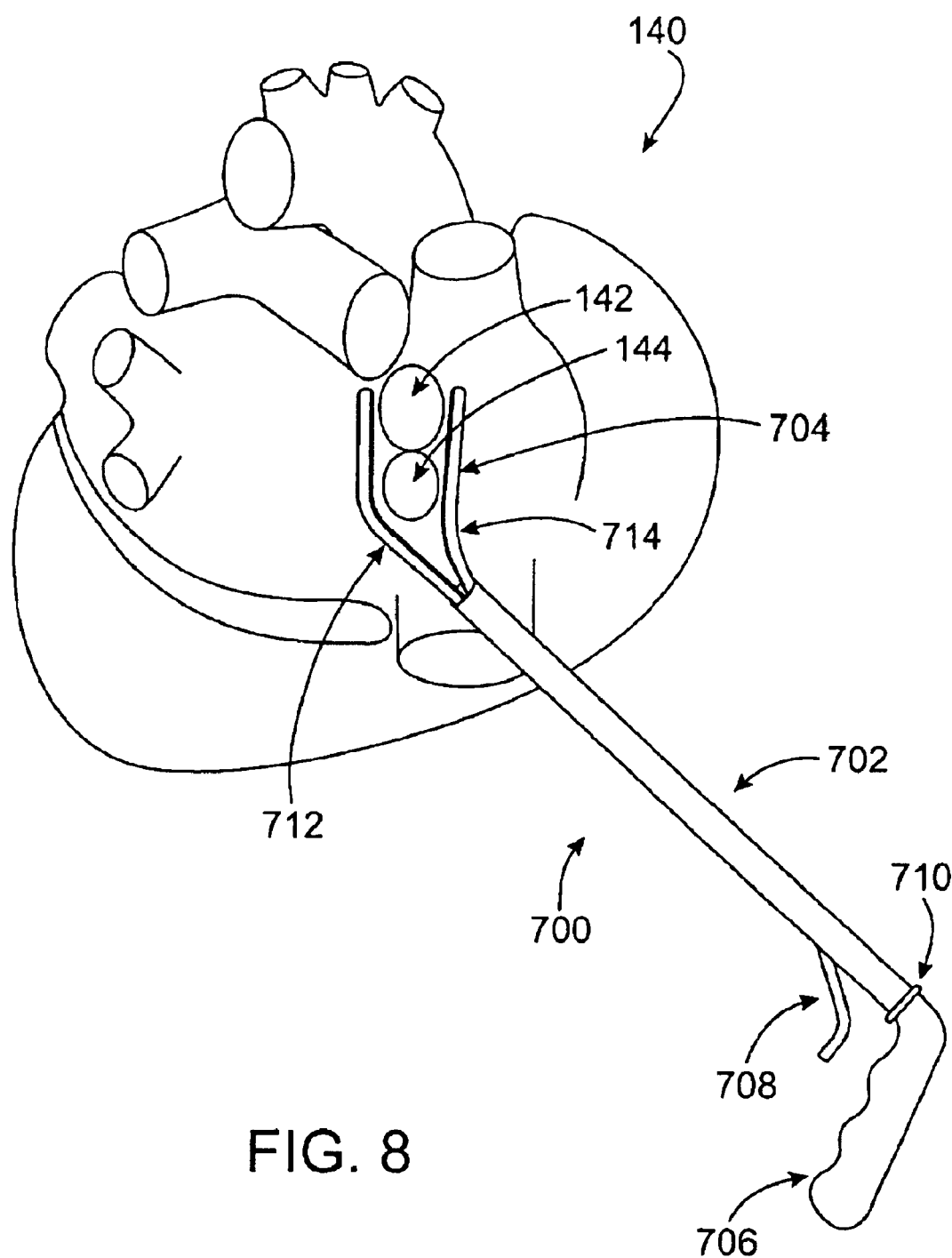
FIG. 8 is a perspective view of a human heart and an elongate shaft ablation device in position for ablating cardiac tissue, according to one embodiment of the invention.

FIG. 8 shows ablation device 700, as just described, in a position for performing an ablation procedure on epicardial tissue of heart 140. Device as shown will ablate in a pattern approximating two lines adjacent the right pulmonary veins 142, 144. It should be understood, from the foregoing descriptions of various embodiments, that jaw member 704 and ablation members 712, 714 could alternatively be configured in any other suitable shape, size or configuration to ablate in other patterns on heart 140. Additionally, device 700 may be moved to a variety of positions to ablate multiple patterns in multiple locations on the epicardial tissue.

Figure 9:
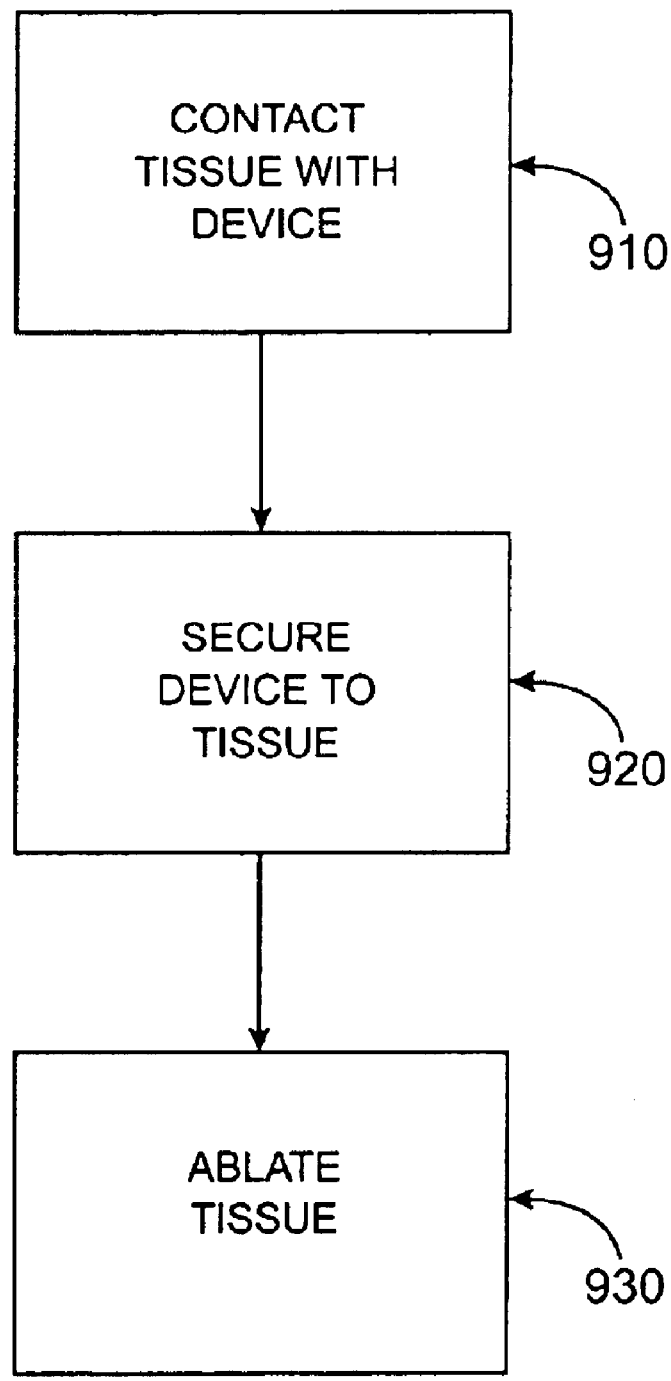
FIG. 9 is a block diagram of a method for ablating tissue according to one embodiment of the invention.

With reference now to FIG. 9, a method for ablating cardiac tissue, such as epicardial tissue, suitably includes contacting cardiac tissue with an ablation device 910, securing the device to the tissue 920 and ablating at least a portion of the contacted, secured tissue 930. Various embodiments of the invention will utilize additional steps or sub-steps of these three basic steps, but it should be emphasized that any additional steps or variations are optional. For example, in some embodiments, contacting the cardiac tissue 910 is preceded by advancing the device into the patient through a minimally invasive introducer device. Contacting the device with the tissue 910 may include positioning the device using a positioning arm or other positioning device. In some embodiments, securing the device to the tissue 920 may also comprise invaginating a portion of epicardial tissue partially within one or more suction apertures and/or may include using one or more suction apertures to dissect through fatty tissue disposed over epicardium. Securing the device 920 may also involve securing with enough force to allow stabilization and/or positioning of the heart itself. And ablation of epicardial tissue 930 may involve ablation in any location or pattern as described above with reference to the inventive devices. Therefore, the descriptions of various methods provided herein are offered for exemplary purposes only and should not be interpreted to limit the scope of the invention as described in the claims.

Other aspects of a method for ablating epicardial tissue may include imaging the epicardial tissue and an area surrounding the tissue to be ablated, using a visualization device. Such a device may be coupled with the ablation device or may be a separate imaging device. In some embodiments, an insufflation device may be inserted between the epicardium and the pericardium and insufflation fluid or gas may be introduced to form a space between the epicardium and pericardium. The space may be used to enhance visualization, allow for freer manipulation of devices near the site for ablation and the like. Another aspect may include sensing ablation of epicardial tissue with one or more sensors, as described above. In some embodiments, tissue may optionally be cooled via a cooling member and/or irrigation of fluid into contact with the tissue. Finally, the actual ablation of epicardial tissue may be accomplished with any suitable ablation member and form of energy, including RF, thermoelectric, cryogenic, microwave, laser, ultrasound or the like. In one embodiment, ablation is achieved and/or enhanced by delivery of one or more drugs to the tissue.

In one embodiment, a method first includes advancing an ablation device through a minimally invasive introducer device into a patient and to a location for ablating epicardial tissue. The device is then contacted with the epicardial tissue and positioned on the tissue with a positioning arm or other device inserted through the same or a separate minimally invasive introducer or incision. Positioning device, in some embodiments, may be a flexible, rigidifying positioner which allows for positioning and then stabilizing with the same device. The ablation device may be placed in any suitable location for ablating epicardial tissue. In one embodiment, for example, ablation device will contact tissue at least partially encircling two pulmonary veins, such as the right superior and right inferior pulmonary veins. The ablation device may contact epicardial tissue directly adjacent the bases of the veins but may be configured to maintain a safe distance between the ablation member on the device and the actual veins.

Once the epicardial tissue is contacted, the device may be secured to the tissue by securing means, such as suction or adhesive. In fact, the device may be secured to the tissue sufficiently in some embodiments to allow the heart to be stabilized and/or positioned using the device and a positioner. For example, a beating heart may be stabilized to reduce or eliminate motion during an ablation procedure or may be pulled, turned or otherwise moved into an advantageous position for ablating, visualizing or treating the heart. Suction force may also be supplied in sufficient strength to dissect through a layer of adipose tissue overlying the epicardial tissue, which may provide improved contact of an ablation member with the epicardial tissue. Once the tissue is secured, at least a portion of the tissue may be ablated by delivering energy to an ablation member (or members) on the device. As already described in detail, such energy may include any suitable energy and may additionally or alternatively include one or more ablative drugs. After ablation, tissue may be cooled via cooling means and/or ablation of tissue may be sensed with one or more sensors. When an ablative procedure is complete, the device may be removed and placed in another location on the heart for an additional procedure or may be removed from the patient altogether.

While the present invention has bee shown and described with reference to various embodiment thereof, the above and other changes in form and detail may be made without departing from the spirit and scope of the invention as defined in the following claims.

What is claimed is:

1. A method for ablating epicardial tissue on a heart of a patient to treat a cardiac arrhythmia, the method comprising:
   contacting epicardial tissue with an ablation device having at least one tissue contacting member coupled with at least one ablation member;
   positioning the ablation device on the epicardial tissue in a position adjacent to at least one pulmonary vein for ablating the tissue to treat the arrhythmia;
   applying sufficient suction force through a plurality of suction apertures aligned on the at least one tissue contacting member to secure the contacting member to the tissue and to cause the at least one ablation member to directly contact the tissue; and
   applying ablation energy to at least a portion of the epicardial tissue with the at least one ablation member to disrupt one or more conduction pathways in the heart, wherein said ablation member is aligned through or between said aligned suction apertures.

2. A method as in claim 1, wherein positioning the ablation device comprises contacting epicardial tissue at least partially encircling at least one pulmonary vein.

3. A method as in claim 2, wherein positioning the ablation device further comprises steering at least one of the tissue contacting member and the ablation member to encircle the at least one pulmonary vein.

4. A method as in claim 1, wherein positioning the ablation device comprises contacting epicardial tissue at least partially encircling all four pulmonary veins.

5. A method as in claim 1, further comprising ablating at least one layer of tissue on the heart underlying the epicardial tissue.

6. A method as in claim 5, wherein ablating the at least one layer comprises ablating a transmural lesion on the heart.

7. A method as in claim 1, further comprising advancing the ablation device through a minimally invasive introducer device to a location for contacting the epicardial tissue.

8. A method as in claim 1, wherein positioning the ablation device comprises:
   positioning the ablation device using at least one flexible positioning arm; and
   applying tensile force to the arm to stiffen the arm.

9. A method as in claim 1, further comprising viewing the epicardial tissue with an imaging device coupled with the ablation device.

10. A method as in claim 1, further comprising:
positioning an insufflation device between the epicardial tissue and a layer of pericardial tissue; and
introducing an insufflation medium into the insufflation device to create a space between the epicardial tissue and the pericardial tissue.

11. A method as in claim 10, wherein the insufflation medium is selected from the group consisting of carbon dioxide, air, helium and a liquid.

12. A method as in claim 10, further comprising positioning an imaging device within the space to view the epicardial tissue.

13. A method as in claim 1, wherein applying ablation energy comprises applying energy through at least one ablation member selected from the group consisting of a radio frequency device, a cryogenic device, an ultrasound device, a laser device, a thermo-electric chip device, a chemical agent delivery device, a biological agent delivery device, a light-activated agent device, a thermal device, a microwave device, and an ablating drug delivery device.

14. A method as in claim 13, wherein applying ablation energy comprises applying energy through at least two bipolar radio frequency electrodes.

15. A method as in claim 13, wherein applying ablation energy comprises applying energy through at least one unipolar radio frequency electrode.

16. A method as in claim 1, further comprising grasping the epicardial tissue between at least two opposable tissue contacting members.

17. A method as in claim 16, wherein applying ablation energy comprises applying radiofrequency energy through a pair of radiofrequency electrodes, a first electrode being coupled with a first opposable tissue contacting member and a second electrode being coupled with a second opposable tissue contacting member.

18. A method as in claim 1, wherein applying sufficient suction force secures the ablation device to the epicardial tissue in a location so as to maintain a margin of safety away from the at least one pulmonary vein.

19. A method as in claim 1, wherein applying sufficient suction force comprises applying suction force in an amount to cause the tissue contacting member to dissect through at least one layer of fat disposed between the tissue contacting member and the epicardium.

20. A method as in claim 1, further comprising adhering the ablation device to the epicardial surface using an adhesive material.

21. A method as in claim 1, further comprising stabilizing the heart using the ablation device.

22. A method as in claim 21, wherein stabilizing the heart comprises securing the ablation device to the epicardial tissue with sufficient force to maintain the tissue in a position to perform an ablation procedure while the heart is beating.

23. A method as in claim 1, further comprising creating a frictional force between at least one textured surface of the at least one tissue contacting member and the epicardial tissue.

24. A method as in claim 1, further comprising sensing an amount of ablation of the epicardial tissue, using at least one sensor coupled with the tissue contacting member so as to contact the epicardial tissue.

25. A method as in claim 24, wherein sensing comprises:
transmitting a radio frequency signal across an area of ablated tissue with at least one transmitting sensor; and
receiving the radio frequency signal with at least one receiving sensor.

26. A method as in claim 25, wherein sensing comprises transmitting and receiving signals between pairs of transmitting and receiving sensors disposed along at least a portion of the tissue contacting member.

27. A method as in claim 1, further comprising cooling at least a portion of the epicardial tissue, using at least one cooling member coupled with the tissue contacting member so as to contact the epicardial tissue.

28. A method as in claim 27, wherein cooling comprises introducing a cooling substance into the cooling member.

29. A method as in claim 1, further comprising using drug delivery means coupled with the tissue contacting member to deliver at least one drug to the epicardial tissue to enhance treatment of the cardiac arrhythmia.

30. A method for ablating epicardial tissue on a heart of a patient to treat a cardiac arrhythmia, the method comprising:
advancing an ablation device through a first minimally invasive incision on the patient;
contacting epicardial tissue with the ablation device;
applying sufficient suction force through a plurality of aligned suction parts on the ablation device to secure the device to the tissue and to cause at least one ablation member of the device to the device to directly contact the tissue; and
applying ablation energy to at least a portion of the epicardial tissue with the at least one ablation member aligned through or between the aligned suction parts to disrupt one or more conduction pathways in the heart.

31. A method as in claim 30, further comprising stabilizing the epicardial tissue using the ablation device.

32. A method as in claim 31, further comprising:
advancing a positioning device to a location near the epicardial tissue through a second minimally invasive incision; and
positioning the ablation device on the epicardial tissue using the positioning device.

33. An ablation device for ablating epicardial tissue on a heart of a patient to treat a cardiac arrhythmia, the ablation device comprising:
at least one tissue contacting member having at least one tissue contacting surface for contacting the epicardial tissue directly adjacent to at least one pulmonary vein, said member comprising a flexible polymer material;
a plurality of suction apertures aligned along at least part of the at least one tissue contacting surface for applying a suction force to secure the ablation device to the epicardial tissue; and
at least one ablation member coupled with the tissue contacting member and aligned through or between the suction apertures for ablating the epicardial tissue to reduce or eliminate the cardiac arrhythmia.

34. A device as in claim 33, wherein the tissue contacting member contacts the epicardial tissue at least partially encircling the at least one pulmonary vein.

35. A device as in claim 34, wherein the tissue contacting member contacts the epicardial tissue at least partially encircling all four pulmonary veins.

36. A device as in claim 33, further comprising a malleable support member coupled with the tissue contacting member.

37. A device as in claim 36, wherein the malleable support member includes at least one protrusion for removably coupling the support member with a positioning device.

38. A device as in claim 36, wherein the malleable support member is sufficiently malleable to allow the device to be introduced into a patient's body through a minimally invasive introducer device or incision.

39. A device as in claim 36, wherein the malleable support member is generally U-shaped.

40. A device as in claim 36, wherein the malleable support member is generally L-shaped.

41. A device as in claim 33, wherein the at least one tissue contacting member comprises two tissue contacting members, each contacting member having a tissue contacting surface, a plurality of suction apertures disposed along the surface and at least one suction port.

42. A device as in claim 41, wherein the two tissue contacting members are coupled with a U-shaped support member.

43. A device as in claim 41, wherein the suction apertures on each tissue contacting member are disposed in a line parallel to a longitudinal axis of each contacting member.

44. A device as in claim 41, wherein the suction apertures on each tissue contacting member are disposed in two lines parallel to, and on either side of, the ablation member.

45. A device as in claim 41, wherein each tissue contacting member further comprises at least one vessel attachment sidearm for attaching to a coronary artery.

46. A device as in claim 33, wherein the suction apertures are configured to allow a portion of the epicardial tissue to be drawn into the aperture when suction is applied.

47. A device as in claim 33, wherein the tissue contacting surface includes a textured surface for enhancing contact of the tissue contacting member with the epicardial tissue.

48. A device as in claim 33, further comprising at least one adhesive substance disposed along the tissue contacting surface.

49. A device as in claim 33, wherein the suction force applied through the at least one suction aperture is sufficient to stabilize the heart while it is beating.

50. A device as in claim 33, wherein the at least one tissue contacting member comprises:
   a flexible elongate body having a tissue contacting surface and a plurality of suction apertures disposed along the surface;
   at least one suction lumen in fluid communication with the suction apertures; and
   at least one suction port for connecting the at least one suction lumen with a source of suction.

51. A device as in claim 50, wherein the plurality of suction apertures is disposed in two parallel rows along the tissue contacting surface, and wherein the ablation member comprises a linear ablation member positioned on the surface between the two rows of suction apertures.

52. A device as in claim 50, wherein the plurality of suction apertures is disposed in one row along the tissue contacting surface, and wherein the ablation member comprises a linear ablation member positioned on the surface along the row.

53. A device as in claim 33, wherein the ablation member comprises an energy transmission member for transmitting energy from an energy source.

54. A device as in claim 53, wherein the energy source is selected from the group consisting of radio frequency energy, ultrasound energy, microwave energy, cryogenic energy, thermoelectric energy and laser energy.

55. A device as in claim 33, wherein the ablation member is approximately U-shaped so as to contact epicardial tissue at least partially encircling the at least one pulmonary vein.

56. A device as in claim 55, wherein the ablation member further comprises at least one partially retractable member such that when the retractable member is deployed the ablation member contacts epicardial tissue completely encircling two pulmonary veins.

57. A device as in claim 33, wherein the ablation member is approximately L-shaped so as to contact epicardial tissue at least partially encircling the at least one pulmonary vein.

58. A device as in claim 33, wherein the ablation member comprises at least one linear ablation member for ablating a linear pattern on epicardial tissue.

59. A device as in claim 58, wherein the at least one linear ablation member comprises a plurality of members, each controllable on a separate radio frequency channel.

60. A device as in claim 33, wherein the ablation member comprises multiple thermoelectric chips disposed in a pattern on the tissue contacting member.

61. A device as in claim 33, further comprising at least one sensor for sensing ablation of the tissue.

62. A device as in claim 61, wherein the at least one sensor senses an electrical depolarization in the epicardial tissue.

63. A device as in claim 61, wherein the at least one sensor is selected from the group consisting of a thermal sensor, an electrical sensor, a thermoelectric sensor, a microchip, a thermistor, a thermocouple and an ultrasonic sensor.

64. A device as in claim 61, wherein the at least one sensor comprises at least one pair of sensors, each pair of sensors positioned on opposite sides of the at least one ablation member.

65. A device as in claim 64, wherein each pair of sensors comprises:
   a first sensor for transmitting a signal across an area of tissue to be ablated; and
   a second sensor for receiving the signal from the first sensor.

66. A device as in claim 33, further comprising at least one cooling member for decreasing heat in the epicardial tissue generated by the ablation member.

67. A device as in claim 66, wherein the cooling member comprises:
   a hollow member adjacent the ablation member; and
   at least one port coupled with the hollow member for allowing introduction of one or more cooling fluids into the hollow member.

68. A device as in claim 67, wherein the at least one hollow member comprises a tubular member.

69. A device as in claim 67, wherein the at least one hollow member comprises a chamber.

70. A device as in claim 67, wherein the at least one port comprises at least one inlet port for allowing the introduction of one or more cooling fluids and at least one outlet port for allowing egress of the one or more cooling fluids from the hollow tubular member.

71. A device as in claim 66, wherein the cooling member comprises:
   a plurality of fluid outlet ports disposed along the at least one tissue contacting member for allowing passage of fluid from the ablation device; and
   at least one fluid inlet port coupled with the fluid outlet ports for allowing introduction of one or more cooling fluids.

72. A device as in claim 33, further comprising visualization means coupled with the device for enhancing visualization of an area around the epicardial tissue to be ablated.

73. A device as in claim 33, further comprising drug delivery means coupled with the tissue contacting member for delivering one or more drugs to the epicardial tissue to enhance treatment of the cardiac arrhythmia.

74. A device as in claim 33, wherein the device is introducible into the patient through a minimally invasive introducer device.

* * * * *